(12) United States Patent
Akita et al.

(10) Patent No.: US 8,808,960 B2
(45) Date of Patent: Aug. 19, 2014

(54) COMPOUND AND CHEMICALLY AMPLIFIED POSITIVE RESIST COMPOSITION

(75) Inventors: Makoto Akita, Hsinchu (TW); Isao Yoshida, Ikeda (JP); Kazuhiko Hashimoto, Toyonaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 404 days.

(21) Appl. No.: 12/719,505

(22) Filed: Mar. 8, 2010

(65) Prior Publication Data
US 2010/0233628 A1   Sep. 16, 2010

(30) Foreign Application Priority Data
Mar. 11, 2009 (JP) ................ 2009-057784

(51) Int. Cl.
*G03F 7/039* (2006.01)
*C08F 32/08* (2006.01)
*C08F 20/30* (2006.01)

(52) U.S. Cl.
USPC ........ 430/270.1; 430/907; 430/910; 430/919; 430/921; 526/280; 526/284; 526/326; 526/328; 526/328.5; 526/334; 560/205; 560/221; 560/227; 560/228

(58) Field of Classification Search
None
See application file for complete search history.

(56) References Cited

U.S. PATENT DOCUMENTS

| | | | | |
|---|---|---|---|---|
| 5,587,274 A | * | 12/1996 | Kishida et al. | ............. 430/270.1 |
| 5,759,739 A | * | 6/1998 | Takemura et al. | ......... 430/270.1 |
| 2002/0147259 A1 | | 10/2002 | Namba et al. | |
| 2003/0113658 A1 | * | 6/2003 | Ebata et al. | ................ 430/270.1 |
| 2003/0235781 A1 | * | 12/2003 | Shida et al. | ................ 430/270.1 |
| 2006/0204888 A1 | * | 9/2006 | Aoki et al. | ................. 430/270.1 |
| 2007/0048662 A1 | * | 3/2007 | Park et al. | .................. 430/270.1 |
| 2008/0241743 A1 | * | 10/2008 | Mizutani et al. | ........... 430/281.1 |

FOREIGN PATENT DOCUMENTS

| | | | |
|---|---|---|---|
| JP | 2001-154359 | * | 6/2001 |
| JP | 2006-330401 A | | 12/2006 |
| JP | 2008-88431 A | | 4/2008 |
| JP | 2008-268740 A | | 11/2008 |
| JP | 2008-268871 A | | 11/2008 |
| JP | 2009-86358 A | | 4/2009 |

OTHER PUBLICATIONS

Machine-assisted English translation of JP2001-154359 provided by JPO (2001).*
Japanese Office Action dated Aug. 6, 2013 for Japanese Application No. 2010-050644.

* cited by examiner

*Primary Examiner* — Sin J. Lee
(74) *Attorney, Agent, or Firm* — Birch, Stewart, Kolasch & Birch, LLP

(57) ABSTRACT

A compound represented by the formula (I):

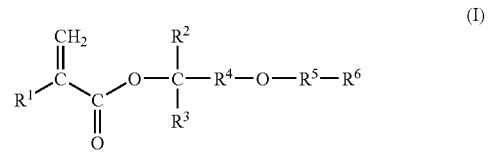

wherein $R^1$ represents a hydrogen atom etc., $R^2$ and $R^3$ each independently represent a hydrogen atom etc., $R^4$ represents a C1-C8 divalent hydrocarbon group, $R^5$ represents a single bond etc., and $R^6$ represents an unsubstituted or substituted C6-C20 aromatic hydrocarbon group, a polymer comprising a structural unit derived from the compound represented by the formula (I) and a chemically amplified positive resist composition comprising the polymer, at least one acid generator and at least one solvent.

10 Claims, No Drawings

COMPOUND AND CHEMICALLY AMPLIFIED POSITIVE RESIST COMPOSITION

This nonprovisional application claims priority under 35 U.S.C. §119(a) on Patent Application No. 2009-057784 filed in JAPAN on Mar. 11, 2009, the entire contents of which are hereby incorporated by reference.

FIELD OF THE INVENTION

The present invention relates to a compound and a chemically amplified positive resist composition.

BACKGROUND OF THE INVENTION

A chemically amplified positive resist composition is used for semiconductor microfabrication employing a lithography process using i-rays, KrF, ArF and electron beam; forming a bump or a thick film resist pattern in the production of semiconductor devices; forming a wiring pattern or a thick film resist laminated body in the production of circuit board; and the like.

It is expected for the chemically amplified resist composition to give patterns having high resolution and good pattern profile.

US 2002/147259 A1 discloses a chemically amplified positive resist composition comprising a resin which comprises a structural unit derived from hydroxystyrene and a structural unit derived from 2-methyl-2-adamantyl methacrylate, and an acid generator.

WO 2006/126433 A1 discloses a chemically amplified positive resist composition comprising a resin which comprises a structural unit derived from 4-hydroxystyrene, a structural unit derived from styrene, a structural unit derived from tert-butyl methacrylate and a structural unit derived from 4-(4-hydroxyphenylsufoxy)phenyl methacrylate, and an acid generator. WO 2006/126433 A1 also discloses a chemically amplified positive resist composition comprising a resin which comprises a structural unit derived from 4-hydroxystyrene, a structural unit derived from 4-(1-ethoxyethoxy)styrene, a structural unit derived from 4-(4-hydroxyphenylsufoxy)phenyl methacrylate and a structural unit derived from 4-[4-(1-ethoxyethoxy)phenylsufoxy]phenyl methacrylate, and an acid generator.

SUMMARY OF THE INVENTION

The present invention relates to the followings:
<1> A compound represented by the formula (I):

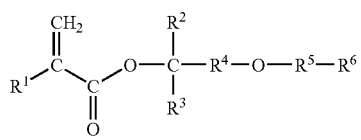

wherein $R^1$ represents a hydrogen atom, a fluorine atom, a C1-C4 linear or branched chain alkyl group or a C1-C4 fluorinated linear or branched chain alkyl group, $R^2$ and $R^3$ each independently represent a hydrogen atom or a C1-C4 linear or branched chain alkyl group, $R^4$ represents a C1-C8 divalent hydrocarbon group, $R^5$ represents a single bond, a C1-C4 divalent hydrocarbon group or a carbonyl group, and $R^6$ represents an unsubstituted or substituted C6-C20 aromatic hydrocarbon group;

<2> The compound according to <1>, wherein the unsubstituted or substituted C6-C20 aromatic hydrocarbon group in $R^6$ is a phenyl group, a naphthyl group, an anthryl group or a phenanthryl group and the phenyl group, the naphthyl group, the anthryl group and the phenanthryl group may have a C1-C6 linear or branched chain alkyl group or a C1-C6 linear or branched chain alkoxy group;

<3> The compound according to <1>, wherein the unsubstituted or substituted C6-C20 aromatic hydrocarbon group in $R^6$ is an anthryl group which may have a C1-C6 linear or branched chain alkyl group or a C1-C6 linear or branched chain alkoxy group;

<4> The compound according to <3>, wherein the anthryl group is a 9-anthryl group;

<5> A polymer comprising a structural unit derived from a compound represented by the formula (I):

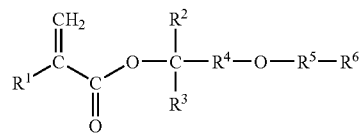

wherein $R^1$ represents a hydrogen atom, a fluorine atom, a C1-C4 linear or branched chain alkyl group or a C1-C4 fluorinated linear or branched chain alkyl group, $R^2$ and $R^3$ each independently represent a hydrogen atom or a C1-C4 linear or branched chain alkyl group, $R^4$ represents a C1-C8 divalent hydrocarbon group, $R^5$ represents a single bond, a C1-C4 divalent hydrocarbon group or a carbonyl group, and $R^6$ represents an unsubstituted or substituted C6-C20 aromatic hydrocarbon group;

<6> The polymer according to <5>, wherein the unsubstituted or substituted C6-C20 aromatic hydrocarbon group in $R^6$ is a phenyl group, a naphthyl group, an anthryl group or a phenanthryl group and the phenyl group, the naphthyl group, the anthryl group and the phenanthryl group may have a C1-C6 linear or branched chain alkyl group or a C1-C6 linear or branched chain alkoxy group;

<7> The polymer according to <5> or <6>, wherein the polymer further comprises a structural unit derived from a styrene having one or more phenolic hydroxyl groups;

<8> The polymer according to <7>, wherein the structural unit derived from a styrene having one or more phenolic hydroxyl groups is a structural unit represented by the formula (II):

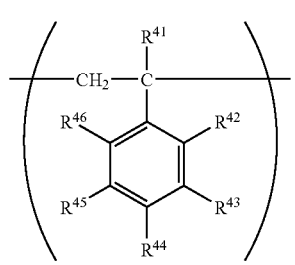

wherein $R^{41}$ represents a hydrogen atom, a fluorine atom, a C1-C4 linear or branched chain alkyl group or a C1-C4 fluorinated linear or branched chain alkyl group, $R^{42}$, $R^{43}$, $R^{44}$, $R^{45}$ and $R^{46}$ each independently represent a hydrogen atom, a hydroxyl group or a C1-C4 linear or branched chain alkyl group, with the proviso that one to three groups among $R^{42}$ to $R^{46}$ are hydroxyl groups and zero to two groups among $R^{42}$ to $R^{46}$ are C1-C4 linear or branched chain alkyl groups;

<11> The polymer according to any one of <5> to <8>, wherein the polymer further comprises a structural unit having an acid-labile group in its side chain;

<10> The polymer according to <9>, wherein the structural unit having an acid-labile group in its side chain is a structural unit represented by the formula (III):

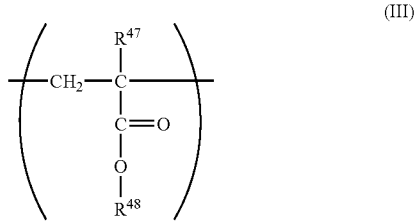

wherein $R^{47}$ represents a hydrogen atom, a fluorine atom, a C1-C4 linear or branched chain alkyl group or a C1-C4 fluorinated linear or branched chain alkyl group, and $R^{48}$ represents a group represented by the following formula:

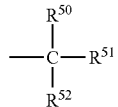

$R^{50}$, $R^{51}$ and $R^{52}$ each independently represent a C1-C6 alkyl group or a C3-C12 alicyclic hydrocarbon group, and $R^{51}$ and $R^{52}$ may be bonded to form a C3-C20 cyclic hydrocarbon group which may be substituted;

<11> The polymer according to any one of <7> to <10>, wherein the content of the structural unit represented by the formula (I) is 0.1 to 50 moles per 100 moles of all the structural units;

<12> A chemically amplified positive resist composition comprising a polymer according to any one of <5> to <11>, at least one acid generator and at least one solvent;

<13> The chemically amplified positive resist composition according to <12>, wherein at least one acid generator comprises a diazomethane compound having a sulfonyl group;

<14> The chemically amplified positive resist composition according to <12> or <13>, wherein the chemically amplified positive resist composition further comprises a basic nitrogen-containing organic compound.

DESCRIPTION OF PREFERRED
EMBODIMENTS

First, the compound represented by the formula (I):

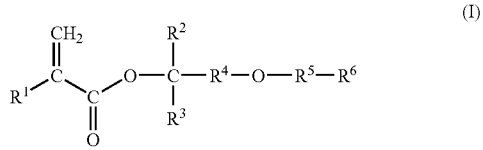

of the present invention is illustrated. The compound represented by the formula (I) is a novel compound.

In the formula (I), $R^1$ represents a hydrogen atom, a fluorine atom, a C1-C4 linear or branched chain alkyl group or a C1-C4 fluorinated linear or branched chain alkyl group.

Examples of the C1-C4 linear or branched chain alkyl group include a methyl group, an ethyl group, a propyl group, an isopropyl group, a butyl group, an isobutyl group, a sec-butyl group and a tert-butyl group, and a methyl group and an ethyl group are preferable, and a methyl group is more preferable.

Examples of the C1-C4 fluorinated linear or branched chain alkyl group include a C1-C4 linear or branched chain perfluoroalkyl group such as a trifluoromethyl group, a pentafluoroethyl group, a heptafluoropropyl group, a heptafluoroisopropyl group, a nonafluorobutyl group, a nonafluoroisobutyl group, a nonafluoro-sec-butyl group and a nonafluoro-tert-butyl group.

$R^1$ is preferably a hydrogen atom or a C1-C4 linear alkyl group, and more preferably a hydrogen atom or a methyl group.

$R^2$ and $R^3$ each independently represent a hydrogen atom or a C1-C4 linear or branched chain alkyl group. Examples of the C1-C4 linear or branched chain alkyl group include the same as described above. $R^2$ and $R^3$ are preferably the same groups and more preferably methyl groups.

$R^4$ represents a C1-C8 divalent hydrocarbon group, and examples thereof include a methylene group, a dimethylene group, a trimethylene group, an ethylidene group, a 1-methyl-1,2-ethylene group, a propylidene group, 1,2-propylene group, an isopropylidene group, a tetramethylene group, a pentamethylene group, a hexamethylene group, an octamethylene group and a 2-methylcyclohexene-3,5-diyl group, and a C1-C4 divalent hydrocarbon group is preferable and a methylene group, a dimethylene group and a trimethylene group are more preferable.

$R^5$ represents a single bond, a C1-C4 divalent hydrocarbon group or a carbonyl group, and examples of the C1-C4 divalent hydrocarbon group include a methylene group, a dimethylene group, a trimethylene group, an ethylidene group, a 1-methyl-1,2-ethylene group, a propylidene group, 1,2-propylene group, an isopropylidene group and a tetramethylene group. $R^5$ is preferably a single bond, a methylene group or a carbonyl group, and more preferably a single bond or a carbonyl group and especially preferably a carbonyl group.

$R^6$ represents an unsubstituted or substituted C6-C20 aromatic hydrocarbon group. Examples of the unsubstituted C6-C20 aromatic hydrocarbon group include a phenyl group, an indenyl group, a naphthyl group, an azurenyl group, a heptalenyl group, a biphenylenyl group, an indacenyl group, an anthryl group, a naphthacenyl group, a phenanthryl group, a fluorenyl group, a 9,10-benzophenanthryl group, a pyrenyl group and a 1,2-benzacenaphthyl group, and a phenyl group, a naphthyl group, an anthryl group and a phenanthryl group are preferable and a phenyl group and an anthryl group are more preferable, and an anthryl group are especially preferable.

Examples of the substituents of the substituted C6-C20 aromatic hydrocarbon group include a C1-C6 linear or branched chain alkyl group such as a methyl group, an ethyl group, a propyl group, an isopropyl group, a butyl group, an isobutyl group, a tert-butyl group, a pentyl group and a hexyl group, and a C1-C6 linear or branched chain alkoxy group such as a methoxy group, an ethoxy group, a propoxy group, an isopropoxy group, a butoxy group, an isobutoxy group, a tert-butoxy group, a pentyloxy group and a hexyloxy group. As the C1-C6 linear or branched chain alkyl group, a methyl group and an ethyl group are preferable, and as the C1-C6 linear or branched chain alkoxy group, a methoxy group is preferable. A C1-C6 linear or branched chain alkyl group is preferable as the substituent. Examples of the substituted C6-C20 aromatic hydrocarbon group include a tolyl group, a xylyl group, a mesityl group and a cumyl group.

$R^6$ is preferably a 9-anthryl group which may have a C1-C6 linear or branched chain alkyl group or a C1-C6 linear or branched chain alkoxy group, and more preferably a 9-anthryl group.

Examples of the compound represented by the formula (I) include the following compounds represented by the formulae (M-1) to (M-192).

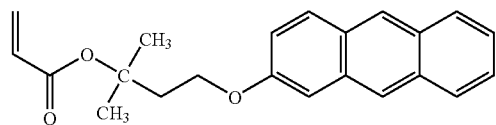
(M-1)

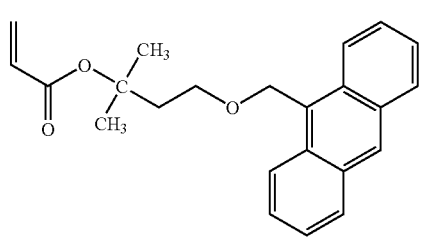
(M-2)

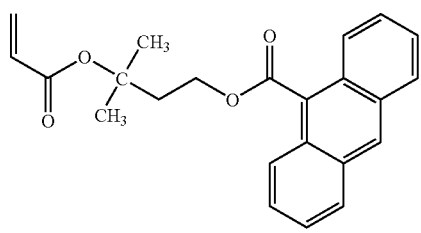
(M-3)

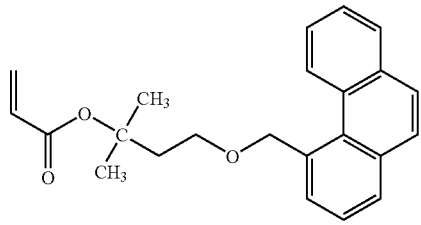
(M-4)

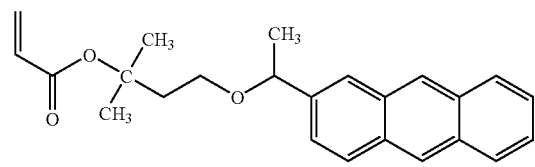
(M-5)

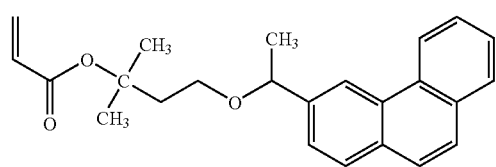
(M-6)

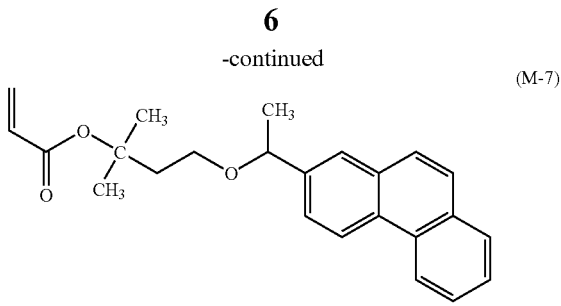
(M-7)

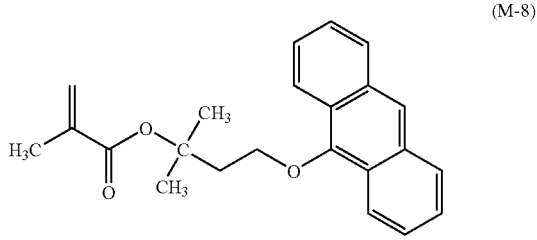
(M-8)

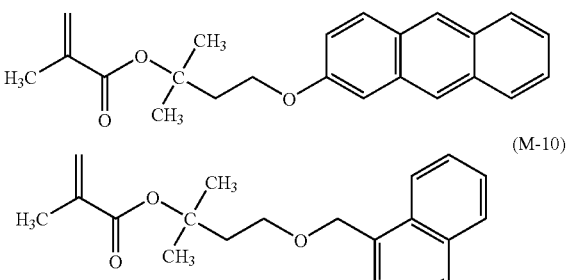
(M-9)

(M-10)

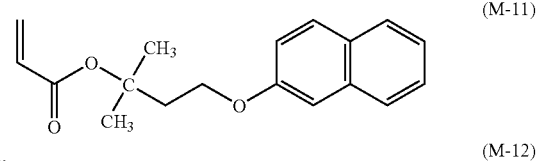
(M-11)

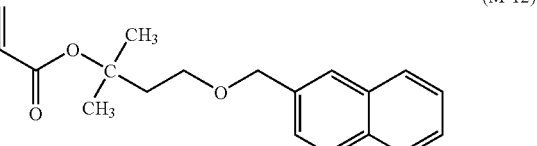
(M-12)

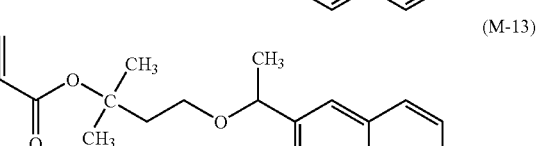
(M-13)

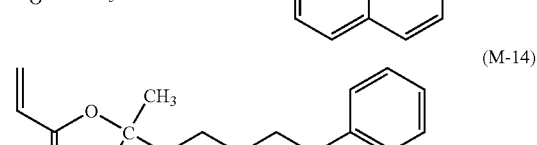
(M-14)

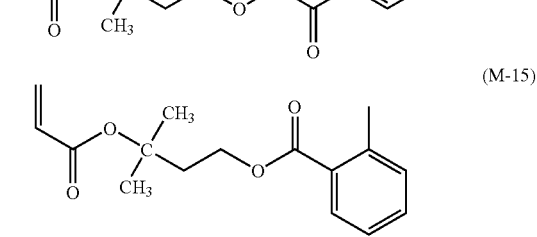
(M-15)

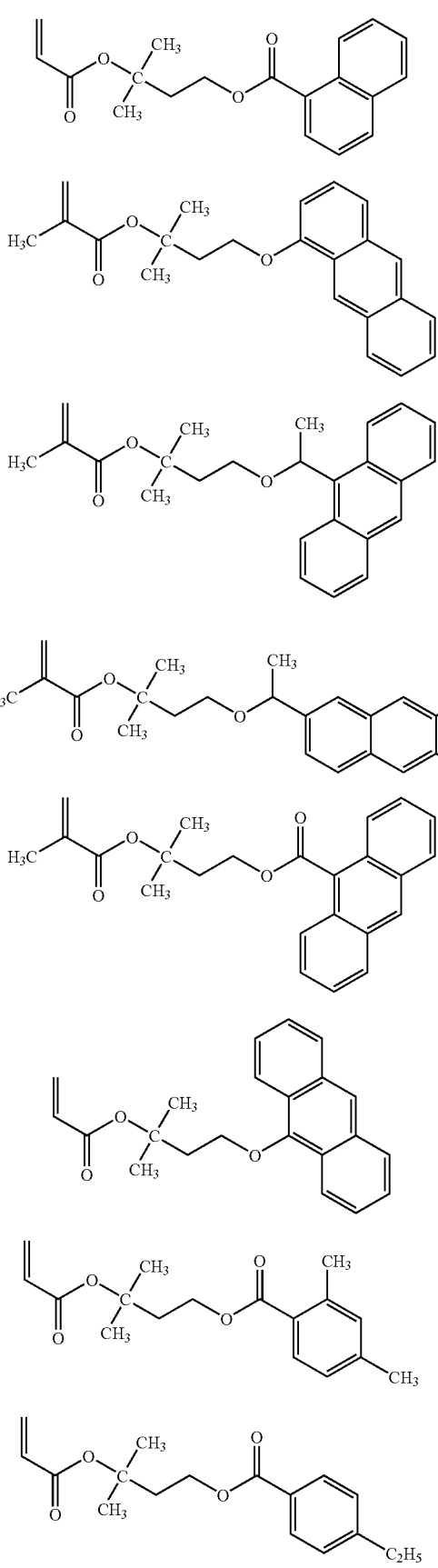

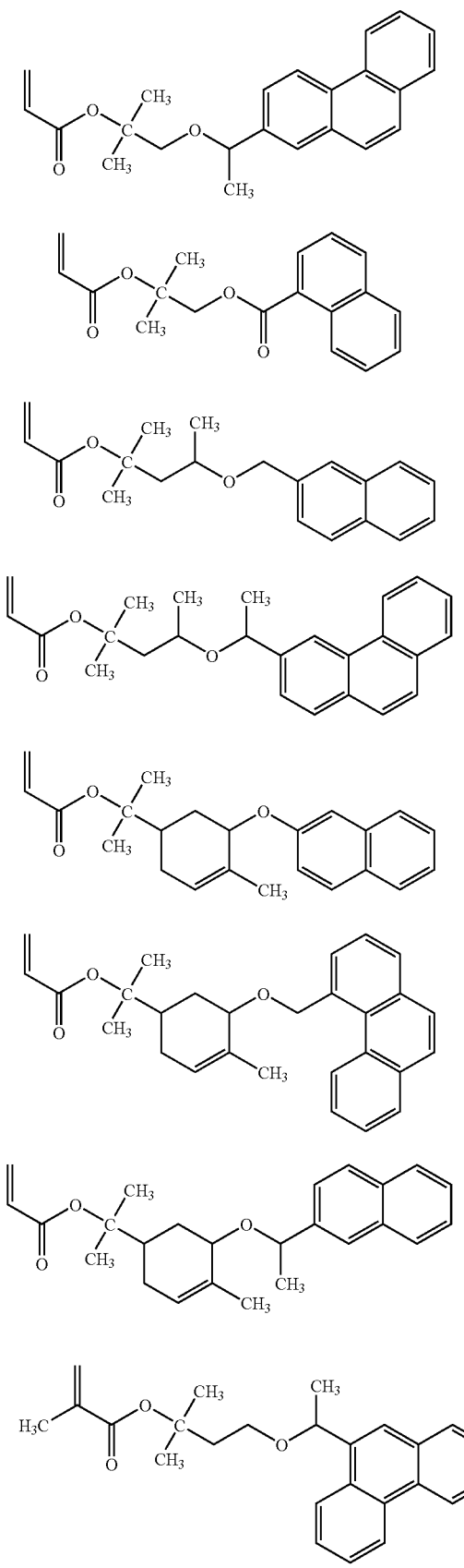
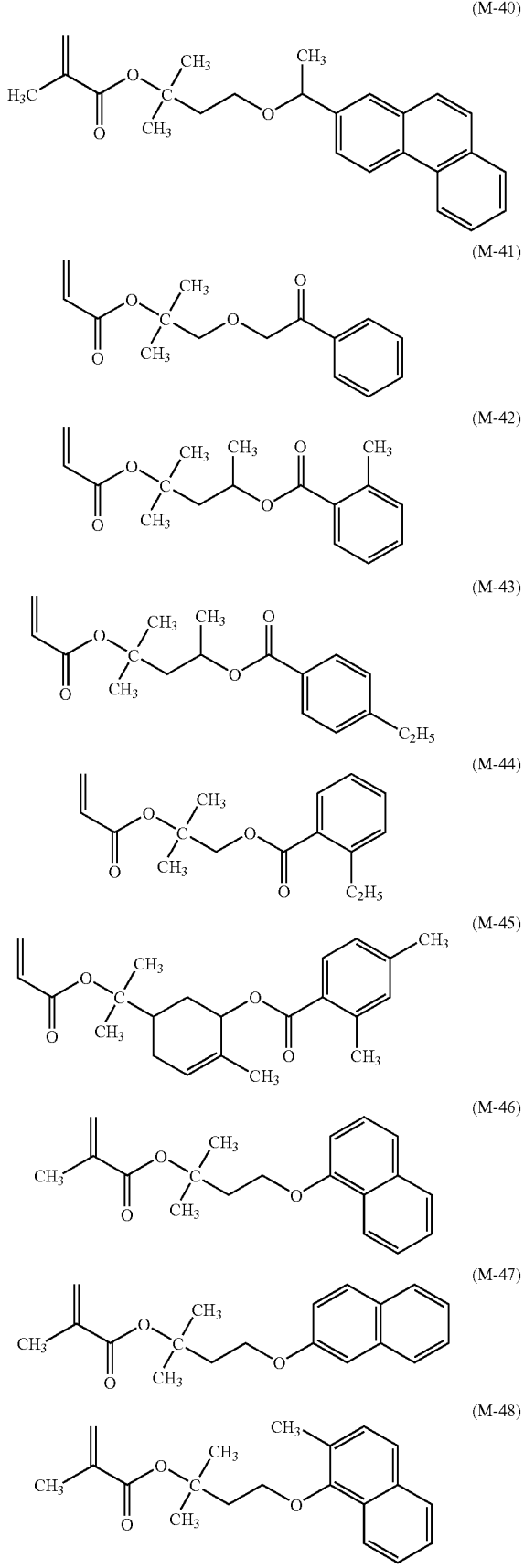

(M-49) 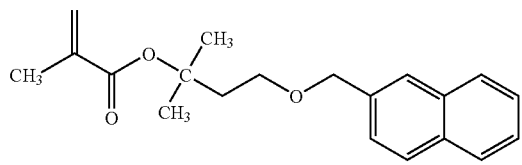
(M-50) 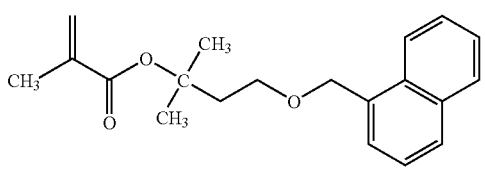
(M-51) 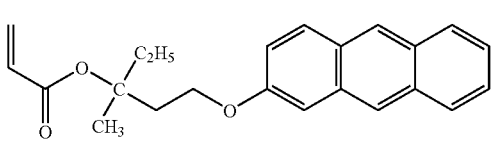
(M-52) 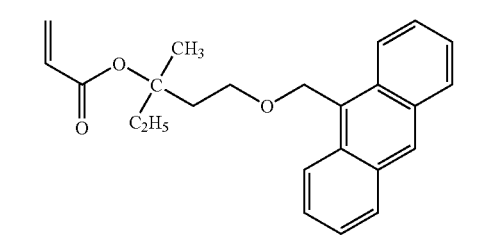
(M-53) 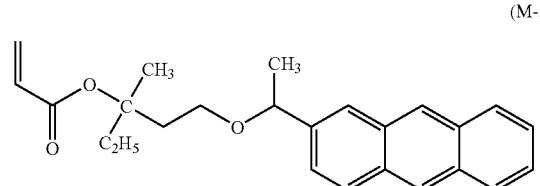
(M-54) 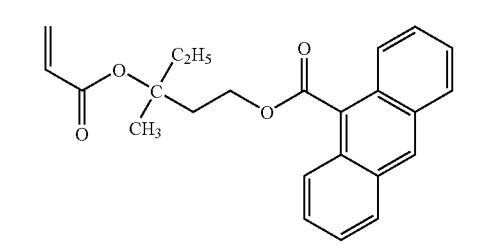
(M-55) 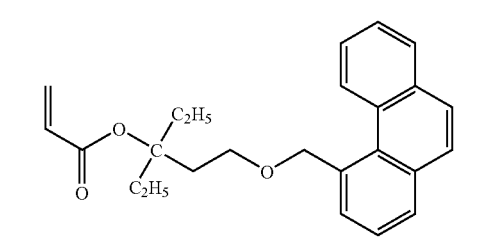
(M-56) 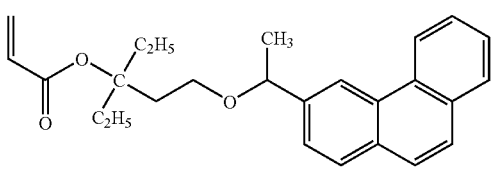
(M-57) 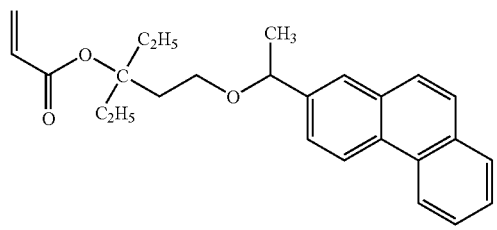
(M-58) 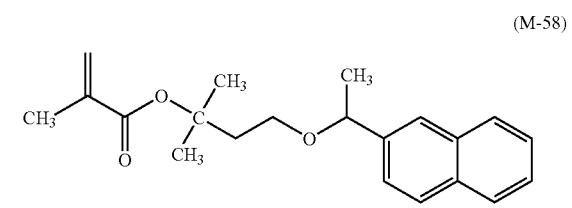
(M-59) 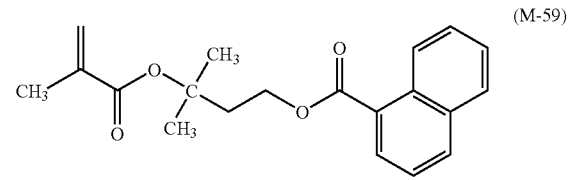
(M-60) 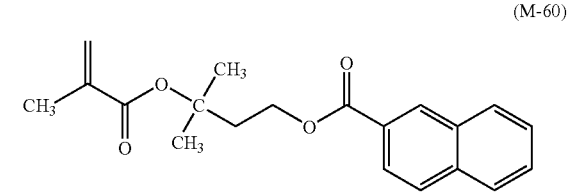
(M-61) 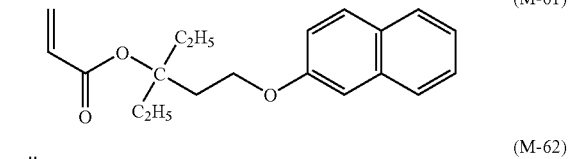
(M-62) 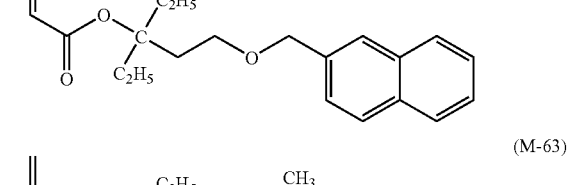
(M-63) 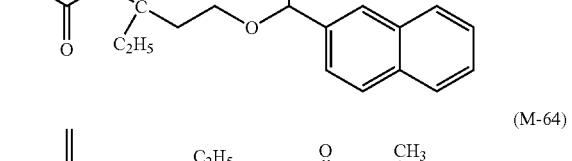
(M-64) 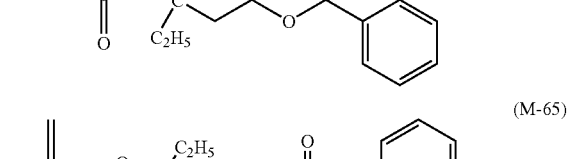
(M-65) 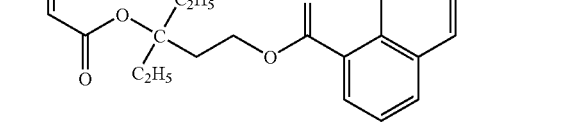

-continued (M-66) (M-67) (M-68) (M-69) (M-70) (M-71) (M-72) (M-73) (M-74) (M-75) (M-76) (M-77) (M-78) (M-79) (M-80) (M-81) (M-82)

-continued (M-83)
(M-84)
(M-85)
(M-86)
(M-87)
(M-88)
(M-89)

-continued (M-90)
(M-91)
(M-92)
(M-93)
(M-94)
(M-95)
(M-96)
(M-97)

(M-98)
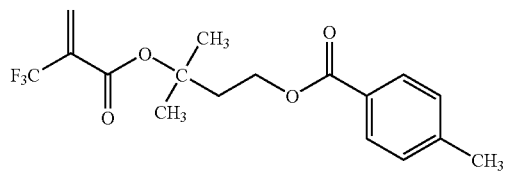
(M-99)
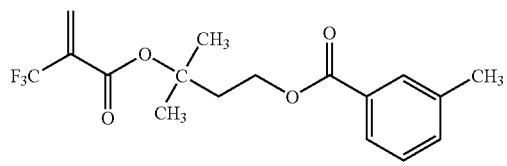
(M-100)
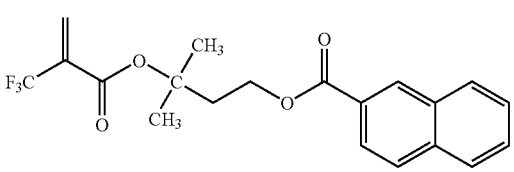
(M-101)
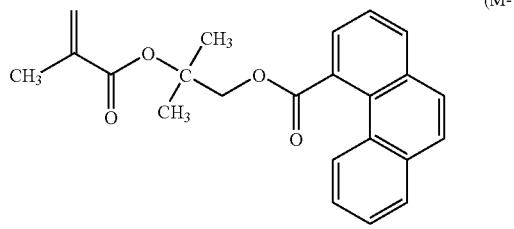
(M-102)
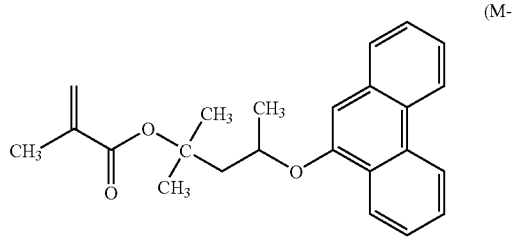
(M-103)
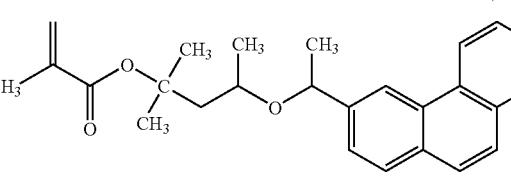
(M-104)
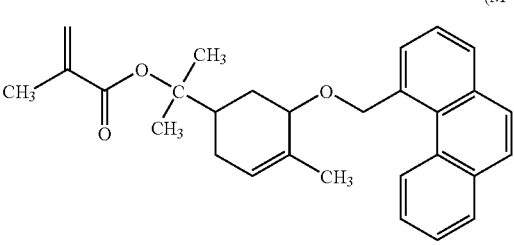
(M-105)
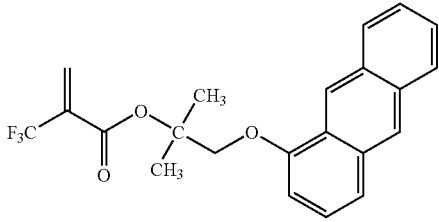
(M-106)
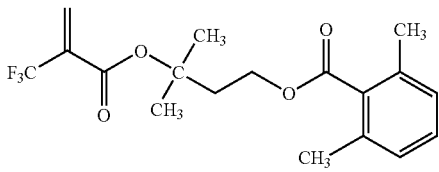
(M-107)
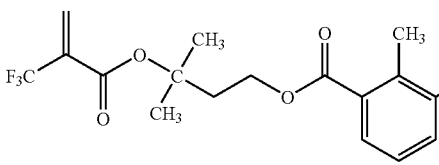
(M-108)
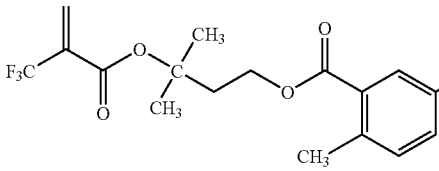
(M-109)
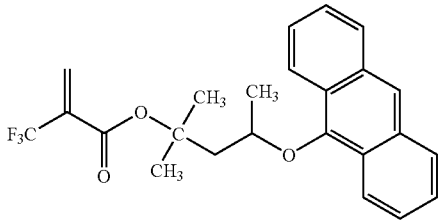
(M-110)
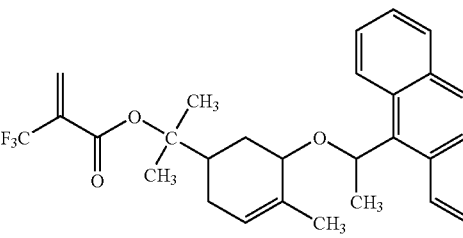
(M-111)
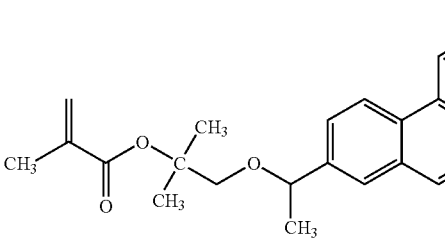

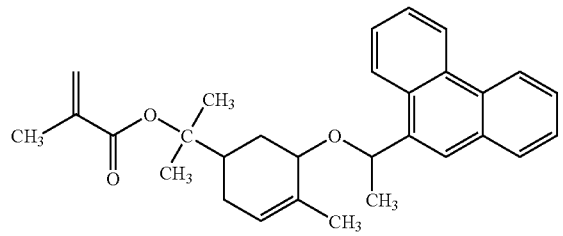
(M-112)
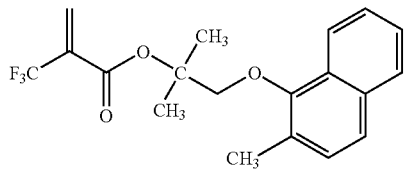
(M-113)
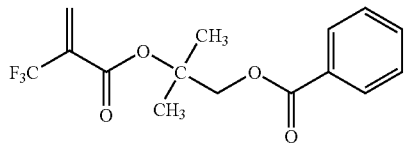
(M-114)
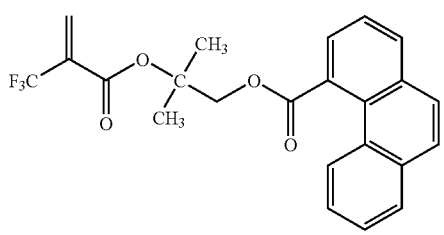
(M-115)
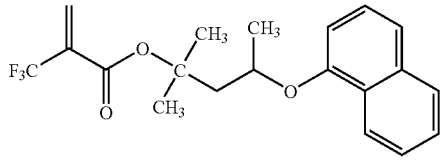
(M-116)
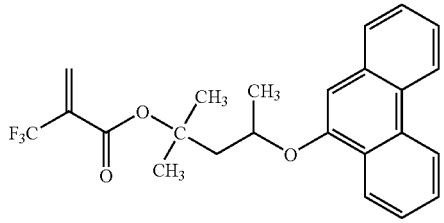
(M-117)
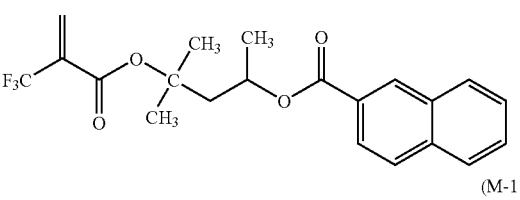
(M-118)
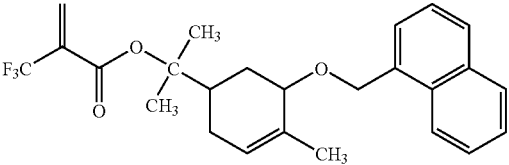
(M-119)
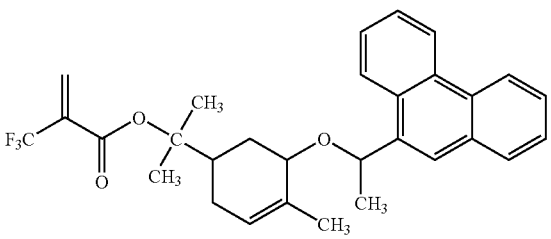
(M-120)
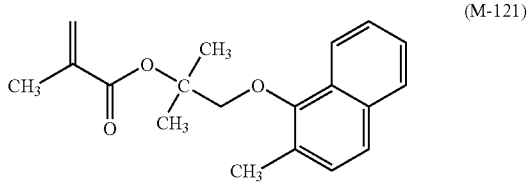
(M-121)
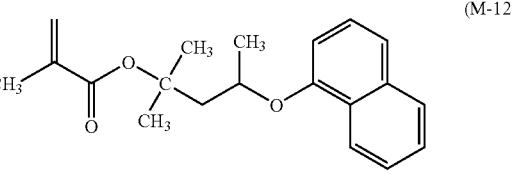
(M-122)
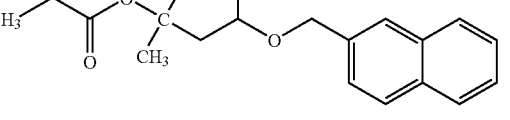
(M-123)
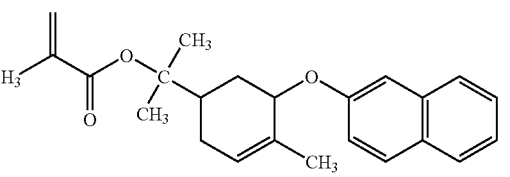
(M-124)
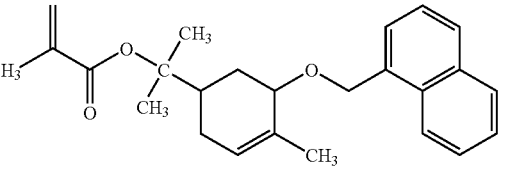
(M-125)
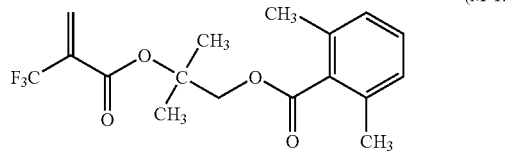
(M-126)
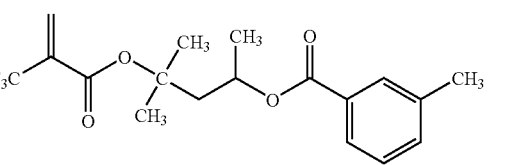
(M-127)

-continued
(M-128)
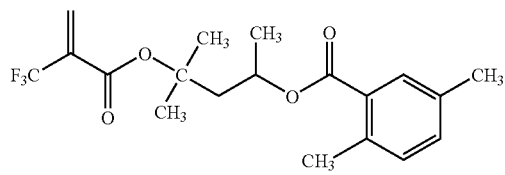
(M-129)
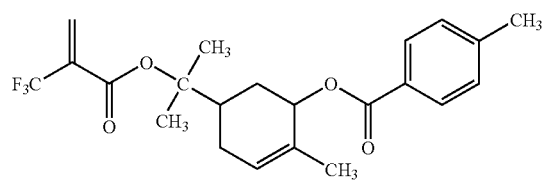
(M-130)
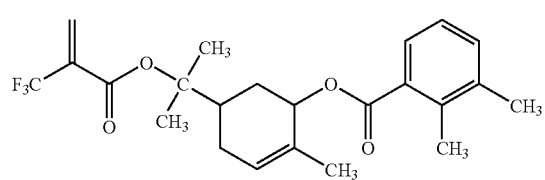
(M-131)
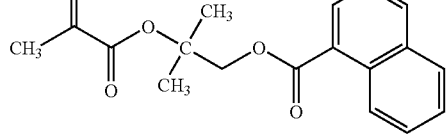
(M-132)
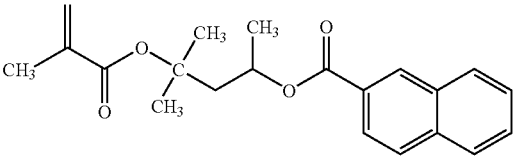
(M-133)
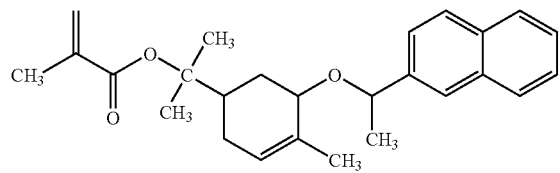
(M-134)
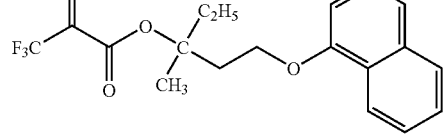
(M-135)
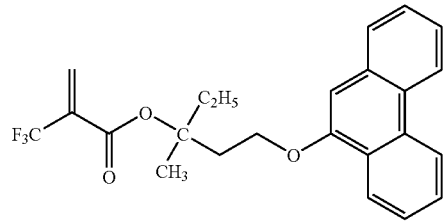
-continued
(M-136)
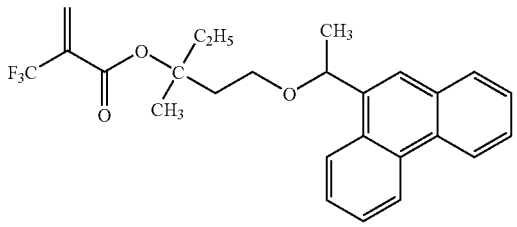
(M-137)
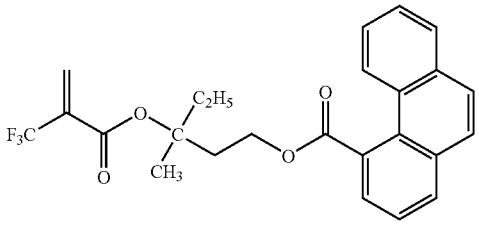
(M-138)
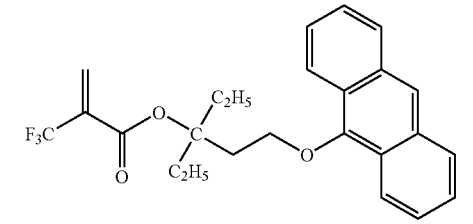
(M-139)
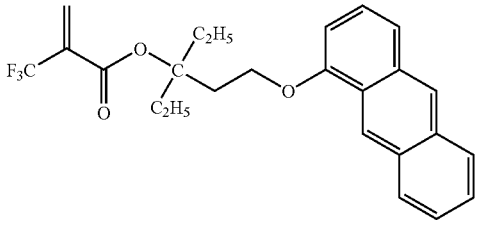
(M-140)
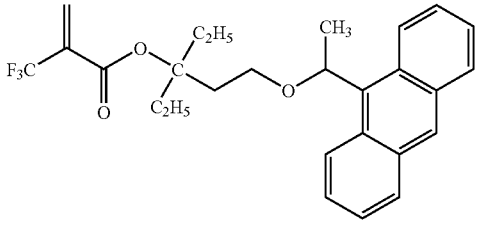
(M-141)
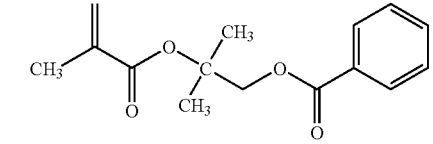
(M-142)
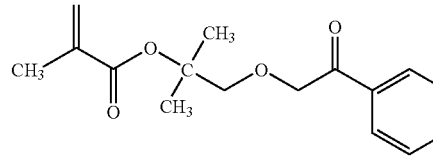

(M-143) 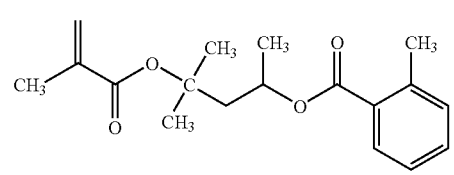
(M-144) 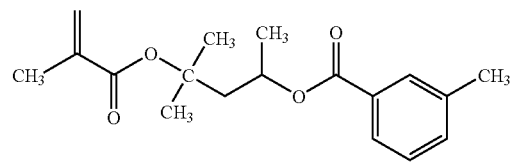
(M-145) 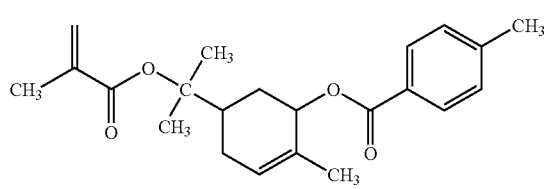
(M-146) 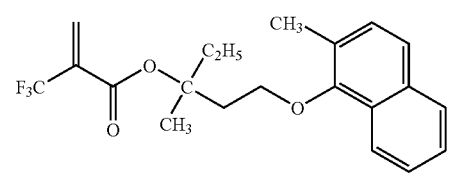
(M-147) 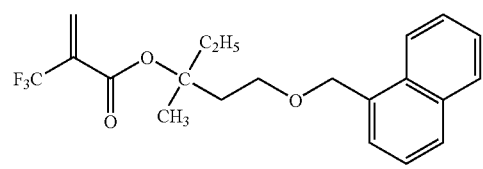
(M-148) 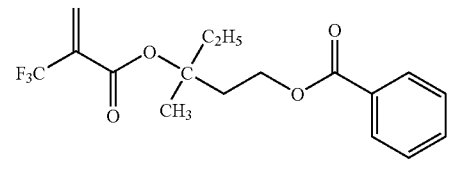
(M-149) 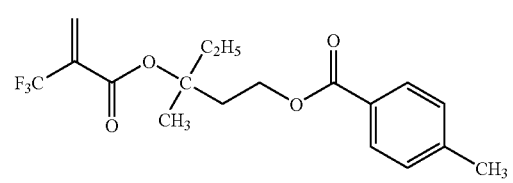
(M-150) 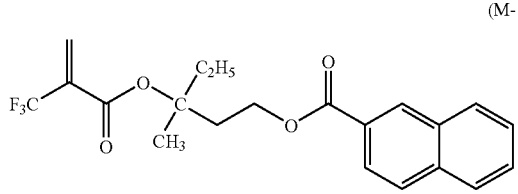
(M-151) 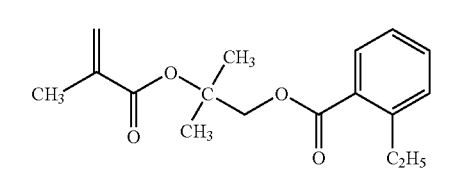
(M-152) 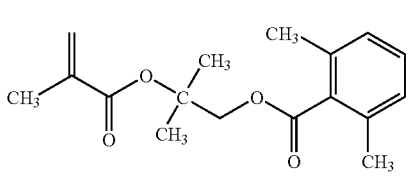
(M-153) 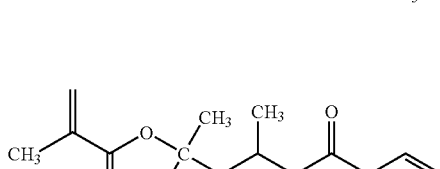
(M-154) 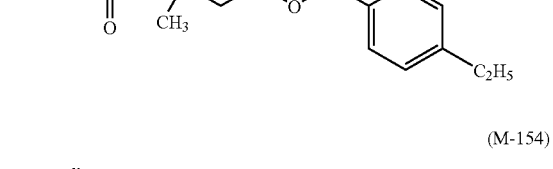
(M-155) 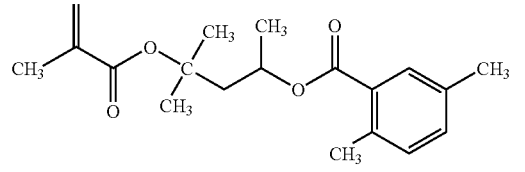
(M-156) 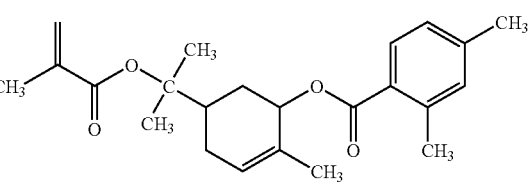
(M-157) 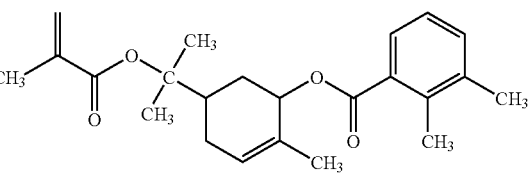
(M-158) 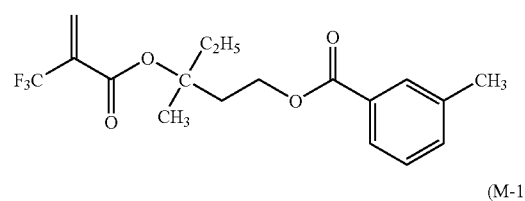
(M-159) 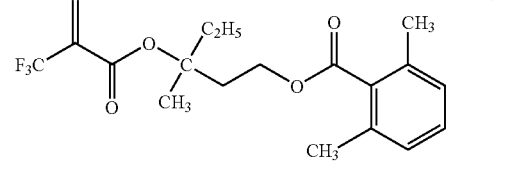
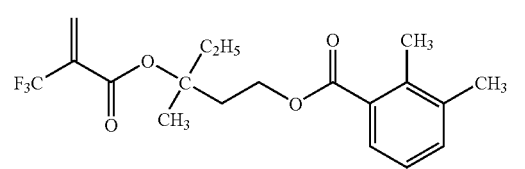

-continued
(M-160) 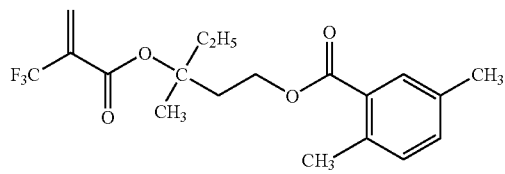
(M-161) 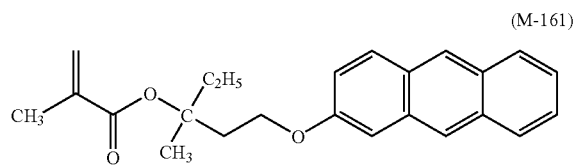
(M-162) 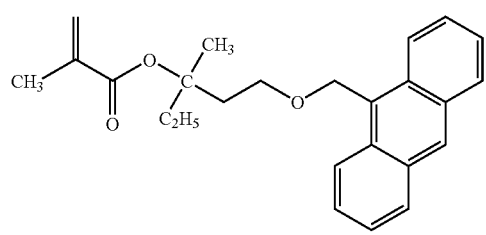
(M-163) 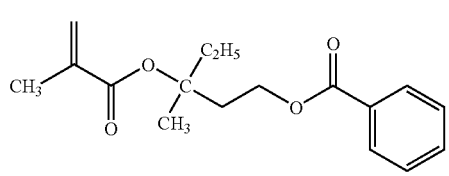
(M-164) 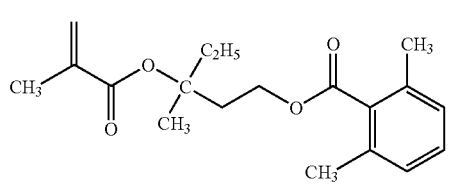
(M-165) 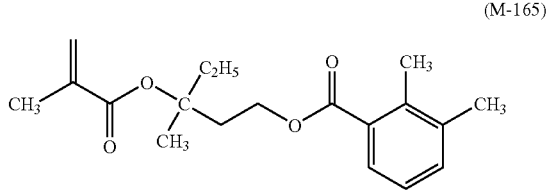
(M-166) 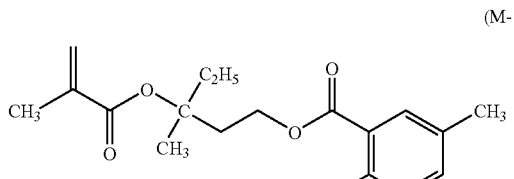
(M-167) 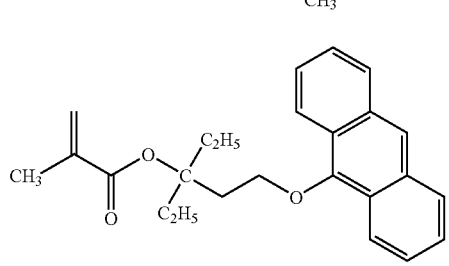
-continued
(M-168)
(M-169)
(M-170)
(M-171)
(M-172)
(M-173)
(M-174)
(M-175)

(M-176)
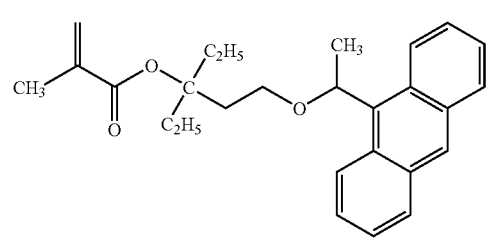
(M-177)
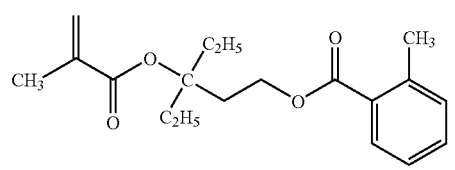
(M-178)
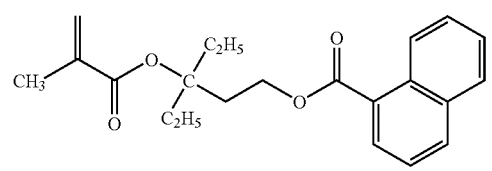
(M-179)
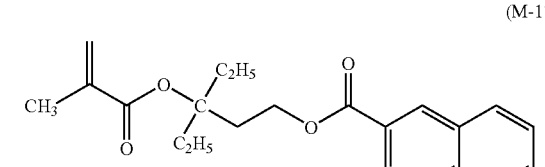
(M-180)
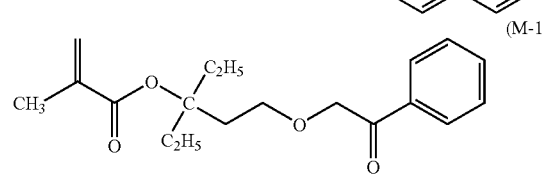
(M-181)
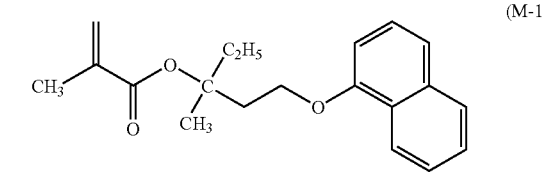
(M-182)
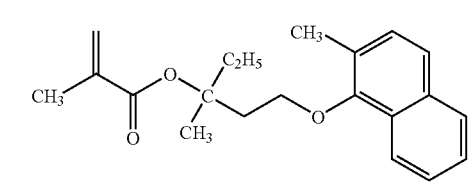
(M-183)
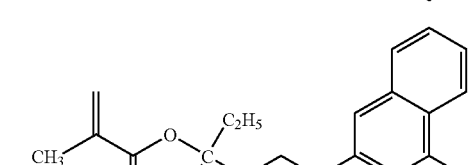
(M-184)
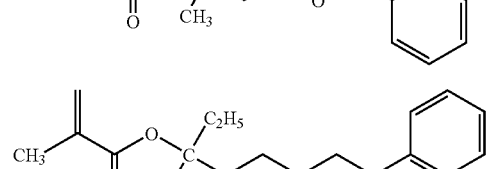
(M-185)
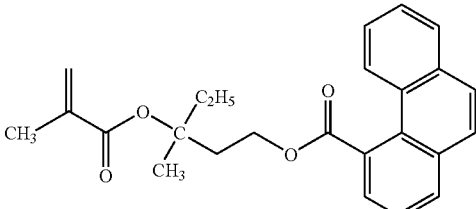
(M-186)
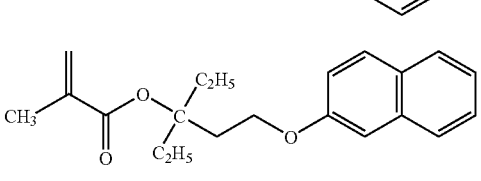
(M-187)
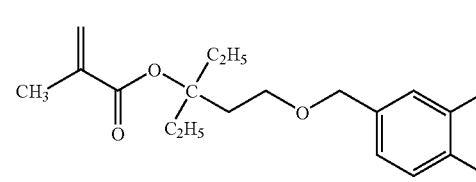
(M-188)
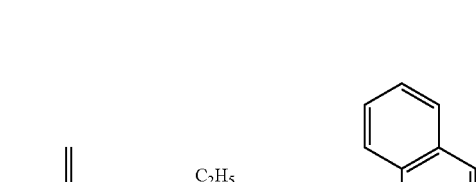
(M-189)
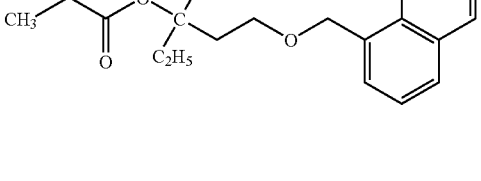
(M-190)
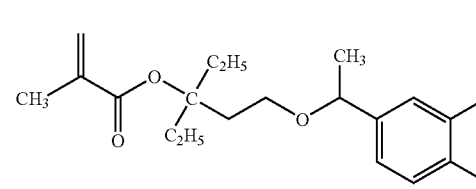
(M-191)
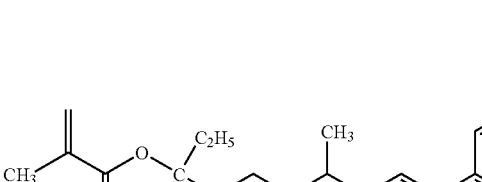

(M-192)

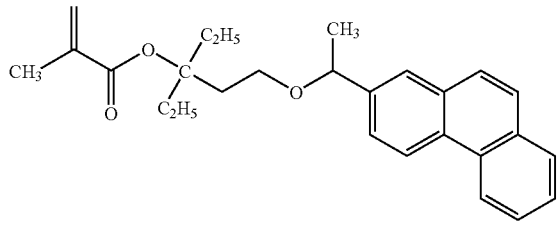

The compound represented by the formula (I) can be produced by reacting a compound represented by the formula (IV):

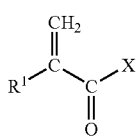

(IV)

wherein R¹ is the same as defined above, and X represents a halogen atom, with an alcohol compound represented by the formula (V):

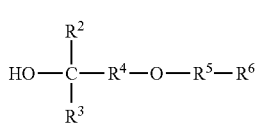

(V)

wherein $R^2$, $R^3$, $R^4$, $R^5$ and $R^6$ are the same as defined above, in an inert solvent such as toluene, tetrahydrofuran, N,N-dimethylformamide, dimethylsulfoxide, acetonitrile, water, methanol, chloroform, dichloromethane and dichloroethane, in the presence of a base at −100 to 150° C., preferably at −20 to 100° C.

In the formula (IV), X represents a halogen atom, and examples of the halogen atom include a fluorine atom, a chlorine atom, a bromine atom and an iodine atom, and a fluorine atom, a chlorine atom and a bromine atom are preferable and a fluorine atom and a chlorine atom are more preferable.

The used amount of the compound represented by the formula (IV) is usually 1 to 5 moles and preferably 1 to 3 moles per 1 mole of the alcohol compound represented by the formula (V).

Examples of the base include an inorganic base such as sodium hydroxide, potassium hydroxide and potassium carbonate, an organic base such as pyridine, triethylamine, lutidine and 1-methylpyrrolidine, and a mixture thereof. The used amount of the base is usually 1 to 5 moles and preferably 1 to 3 moles per 1 mole of the alcohol compound represented by the formula (V).

The obtained compound represented by the formula (I) by the process above can be isolated by extraction and concentration, and it can be further purified by recrystallization, distillation or column chromatography.

The compound represented by the formula (I) can be also produced by reacting the alcohol compound represented by the formula (V) with a compound represented by the formula (VI):

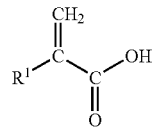

(VI)

wherein R¹ is the same as defined above.

The reaction of the alcohol compound represented by the formula (V) and the compound represented by the formula (VI) is usually carried out by mixing them in an aprotic solvent such as dichloroethane, toluene, ethylbenzene, monochlorobenzene, acetonitrile and N,N-dimethylformamide, at 20 to 200° C., preferably 50 to 150° C. In this reaction, an acid catalyst may be used, and examples of the acid catalyst include organic acids such as p-toluenesulfonic acid, and inorganic acids such as sulfuric acid. This reaction may be conducted with dehydration since the reaction time tends to be shortened. Dehydration may be conducted using a Dean and Stark apparatus, and may be conducted in the presence of a dehydrating agent such as 1,1-carbonyldiimidazole and N,N'-dicyclohexylcarbodiimide.

The used amount of the compound represented by the formula (VI) is usually 0.2 to 3 moles and preferably 0.5 to 2 moles per 1 mole of the alcohol compound represented by the formula (V).

When the acid catalyst is used, the used amount thereof may be catalytic amount or the amount equivalent to solvent, and is usually 0.001 to 5 moles per 1 mole of the alcohol compound represented by the formula (V).

Next, the polymer comprising a structural unit derived from a compound represented by the formula (I) is illustrated. The polymer is novel polymer.

The polymer comprising a structural unit derived from a compound represented by the formula (I) wherein the unsubstituted or substituted C6-C20 aromatic hydrocarbon group in R⁶ is a phenyl group, a naphthyl group, an anthryl group or a phenanthryl group and the phenyl group, the naphthyl group, the anthryl group and the phenanthryl group may have a C1-C6 linear or branched chain alkyl group or a C1-C6 linear or branched chain alkoxy group, is preferable.

The polymer may further comprise a structural unit derived from a styrene having one or more phenolic hydroxyl groups in addition to the structural unit derived from a compound represented by the formula (I). The polymer preferably further comprises a structural unit derived from a styrene having one or more phenolic hydroxyl groups in addition to the structural unit derived from a compound represented by the formula (I).

Examples of the structural unit derived from a styrene having one or more phenolic hydroxyl groups include a structural unit represented by the formula (II):

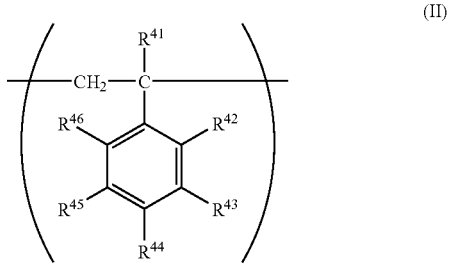

(II)

wherein $R^{41}$ represents a hydrogen atom, a fluorine atom, a C1-C4 linear or branched chain alkyl group or a C1-C4 fluorinated linear or branched chain alkyl group, $R^{42}$, $R^{43}$, $R^{44}$, $R^{45}$ and $R^{46}$ each independently represent a hydrogen atom, a hydroxyl group or a C1-C4 linear or branched chain alkyl group, with the proviso that one to three groups among $R^{42}$ to $R^{46}$ are hydroxyl groups and zero to two groups among $R^{42}$ to $R^{46}$ are C1-C4 linear or branched chain alkyl groups.

Examples of the C1-C4 linear or branched chain alkyl group and the C1-C4 fluorinated linear or branched chain alkyl group include the same as described above, respectively.

The structural unit represented by the formula (II) wherein $R^{42}$, $R^{43}$, $R^{44}$, $R^{45}$ and $R^{46}$ each independently represent a hydrogen atom or a hydroxyl group, with the proviso that one to three groups among $R^{42}$ to $R^{46}$ are hydroxyl groups, is preferable, and the structural unit represented by the formula (II) wherein $R^{42}$, $R^{43}$, $R^{44}$, $R^{45}$ and $R^{46}$ each independently represent a hydrogen atom or a hydroxyl group, with the proviso that one or two groups among $R^{42}$ to $R^{46}$ are hydroxyl groups, is more preferable, and the structural unit represented by the formula (II) wherein $R^{42}$, $R^{43}$, $R^{44}$, $R^{45}$ and $R^{46}$ each independently represent a hydrogen atom or a hydroxyl group, with the proviso that one group among $R^{42}$ to $R^{46}$ is a hydroxyl group, is especially preferable.

Examples of the structural unit represented by the formula (II) include the followings.

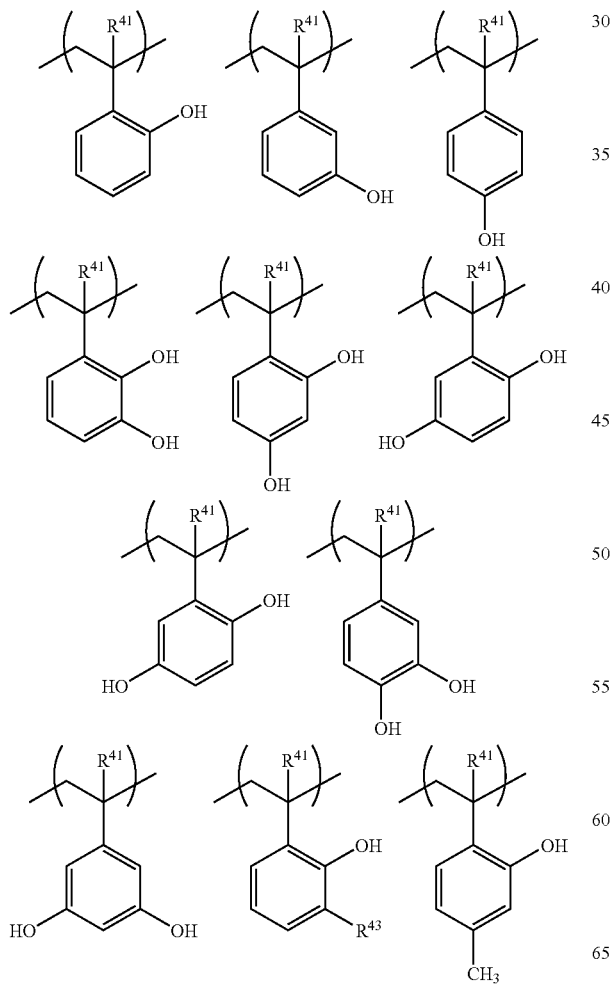

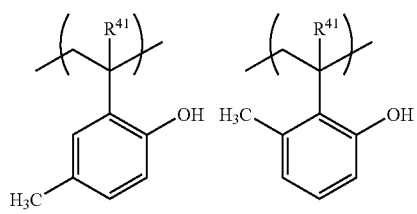

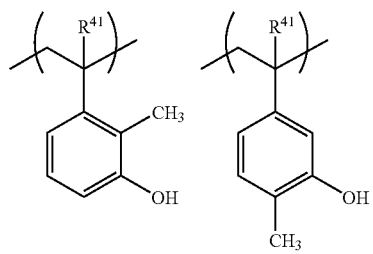

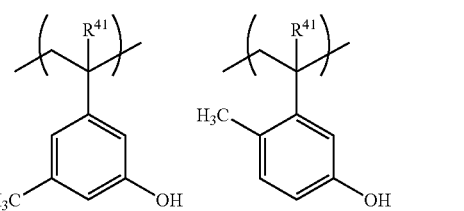

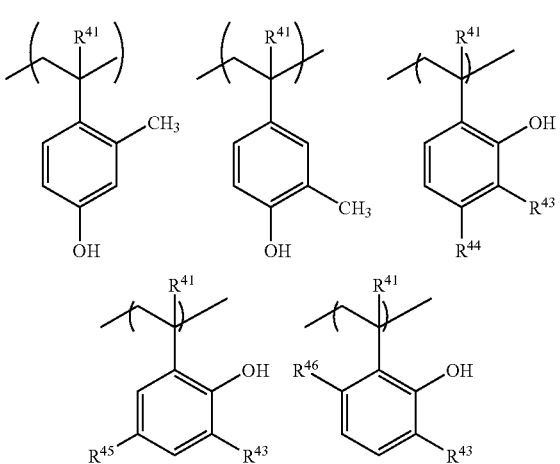

33
-continued
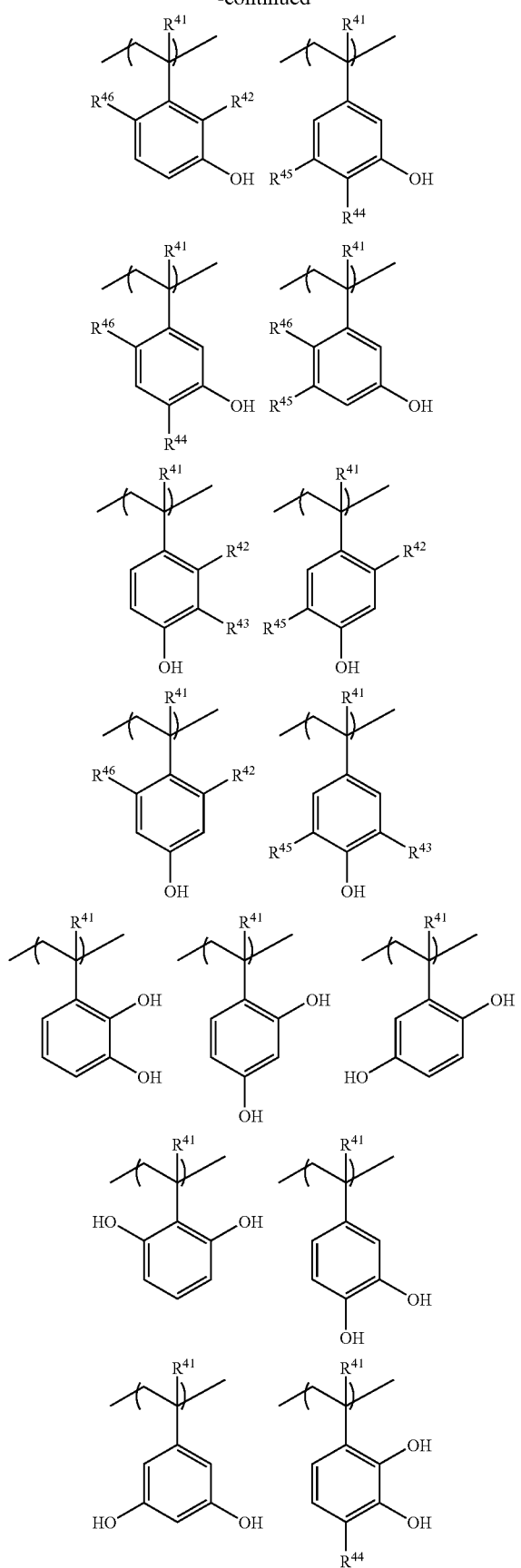
34
-continued
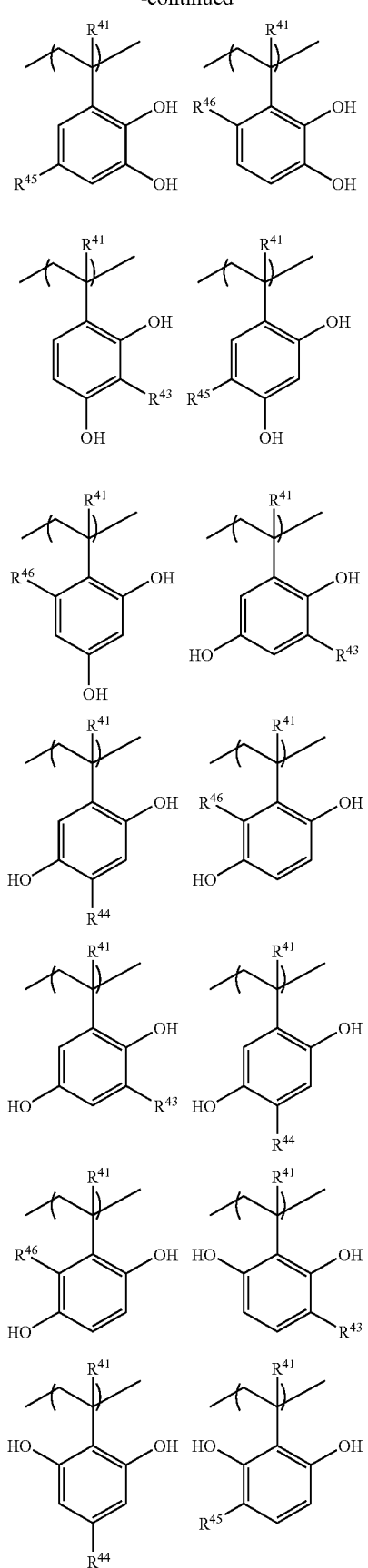

-continued
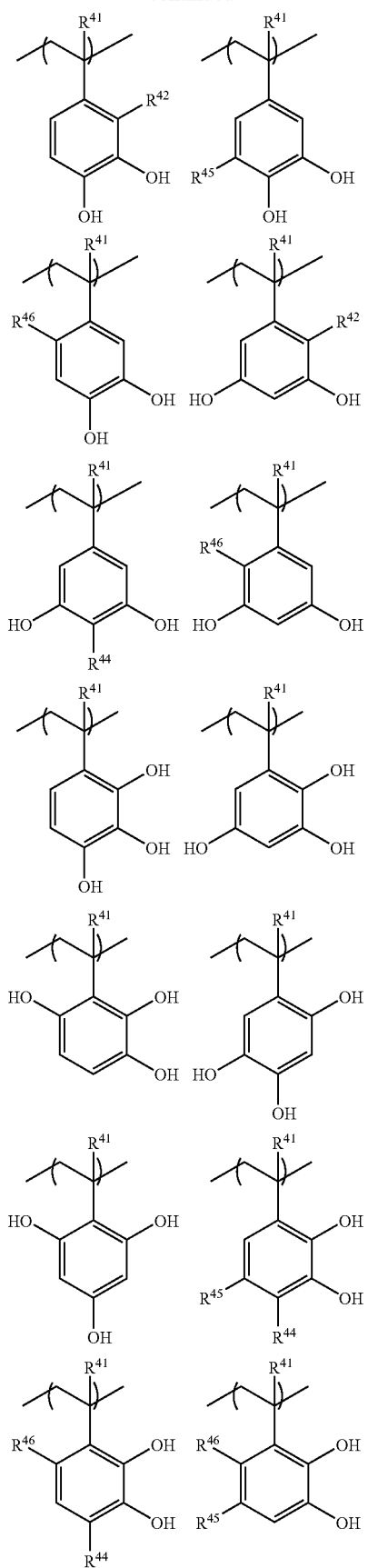
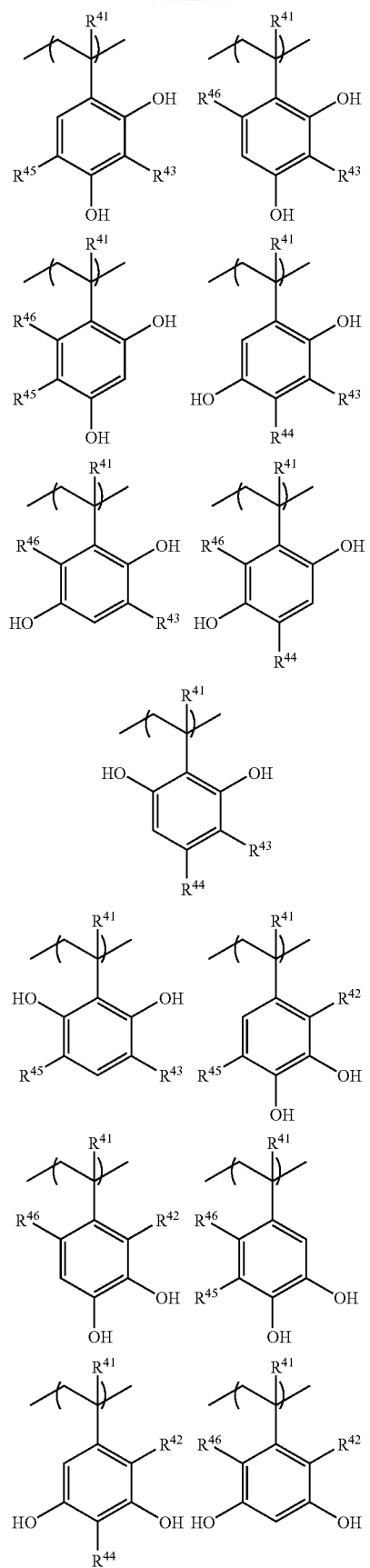

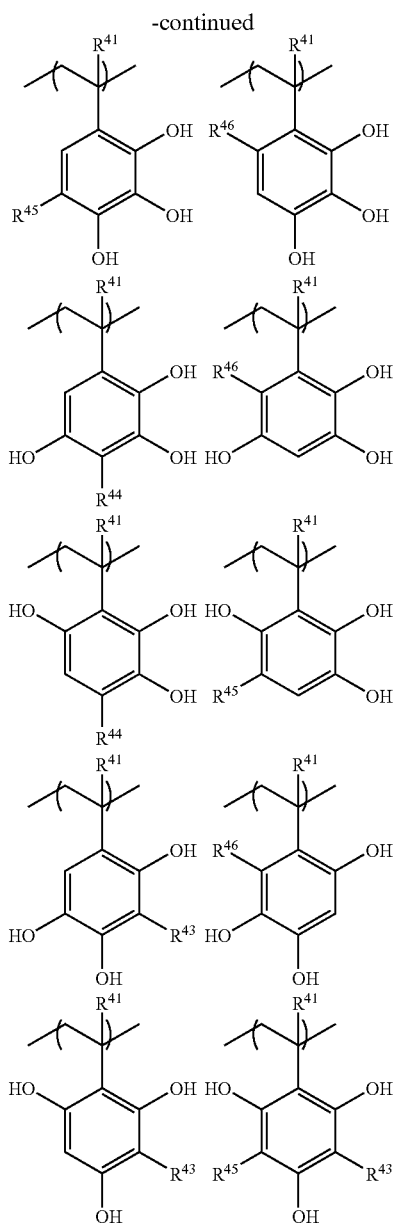

In the above formulae, $R^{41}$, $R^{42}$, $R^{43}$, $R^{44}$, $R^{45}$ and $R^{46}$ are the same as defined above.

A structural unit derived from hydroxystyrene is preferable and a structural unit derived from 4-hydroxystyrene is more preferable.

The polymer may further comprise a structural unit having an acid-labile group in its side chain in addition to the structural unit derived from the compound represented by the formula (I). The polymer preferably further comprises a structural unit having an acid-labile group in its side chain in addition to the structural unit derived from the compound represented by the formula (I).

Preferable polymer comprises the structural unit derived from the compound represented by the formula (I), the structural unit derived from a styrene having one or more phenolic hydroxyl group and the structural unit having an acid-labile group in its side chain.

In this specification, "an acid-labile group" means a group capable to eliminate by the action of an acid.

In the present specification, "ester group" means "a structure having ester of carboxylic acid". Specifically, "tert-butyl ester group" is "a structure having tert-butyl ester of carboxylic acid", and may be described as "—COOC(CH$_3$)$_3$".

Examples of the acid-labile group include a structure having ester of carboxylic acid such as an alkyl ester group in which a carbon atom adjacent to the oxygen atom is quaternary carbon atom, an alicyclic ester group in which a carbon atom adjacent to the oxygen atom is quaternary carbon atom, and a lactone ester group in which a carbon atom adjacent to the oxygen atom is quaternary carbon atom. The "quaternary carbon atom" means a "carbon atom joined to four substituents other than hydrogen atom".

Examples of the acid-labile group include an alkyl ester group in which a carbon atom adjacent to the oxygen atom is quaternary carbon atom such as a tert-butyl ester group; an acetal type ester group such as a methoxymethyl ester, ethoxymethyl ester, 1-ethoxyethyl ester, 1-isobutoxyethyl ester, 1-isopropoxyethyl ester, 1-ethoxypropoxy ester, 1-(2-methoxyethoxy)ethyl ester, 1-(2-acetoxyethoxy)ethyl ester, 1-[2-(1-adamantyloxy)ethoxy]ethyl ester, 1-[2-(1-adamantanecarbonyloxy)ethoxy]ethyl ester, tetrahydro-2-furyl ester and tetrahydro-2-pyranyl ester group; an alicyclic ester group in which a carbon atom adjacent to the oxygen atom is quaternary carbon atom such as an isobornyl ester, 1-alkylcycloalkyl ester, 2-alkyl-2-adamantyl ester, and 1-(1-adamantyl)-1-alkylalkyl ester group.

The preferable structural unit having an acid-labile group in its side chain is a structural unit represented by the formula (III):

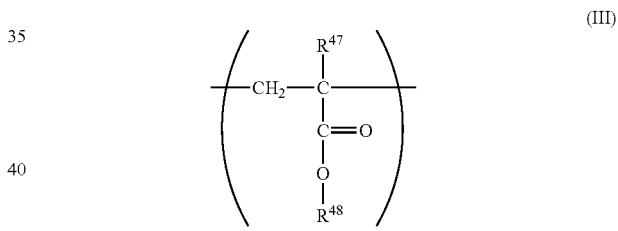

wherein $R^{47}$ represents a hydrogen atom, a fluorine atom, a C1-C4 linear or branched chain alkyl group or a C1-C4 fluorinated linear or branched chain alkyl group, and $R^{48}$ represents a group represented by the following formula:

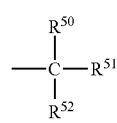

$R^{50}$, $R^{51}$ and $R^{52}$ each independently represent a C1-C6 alkyl group or a C3-C12 alicyclic hydrocarbon group, and $R^{51}$ and $R^{52}$ may be bonded to form a C3-C20 cyclic hydrocarbon group which may be substituted.

Examples of the C1-C4 linear or branched chain alkyl group and the C1-C4 fluorinated linear or branched chain alkyl group include the same as described above. Examples of the C1-C6 alkyl group include the above mentioned C1-C4 alkyl group, a pentyl group and a hexyl group. Examples of the C3-C12 alicyclic hydrocarbon group include a cyclopentyl group, a cyclohexyl group, a norbornyl group, a methylcyclopentyl group, a methylcyclohexyl group, dimethylcyclohexyl group and a methylnorbornyl group. Examples of the C3-C20 cyclic hydrocarbon group include an adamantyl group.

$R^{47}$ is preferably a hydrogen atom, a methyl group or a trifluoromethyl group, and more preferably a hydrogen atom or a methyl group.

As the structural unit represented by the formula (III), a structural unit represented by the formula (IIIa):

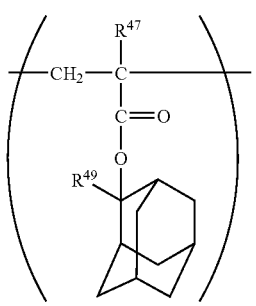

(IIIa)

wherein $R^{47}$ is the same as defined above and $R^{49}$ represents a C1-C8 linear or branched chain alkyl group, is preferable.

Preferable examples of the C1-C8 linear or branched chain alkyl group include a methyl group, an ethyl group and an isopropyl group.

Examples of the polymer include a polymer comprising a structural units represented by the formulae (i) and (ii):

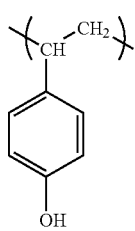

(i)

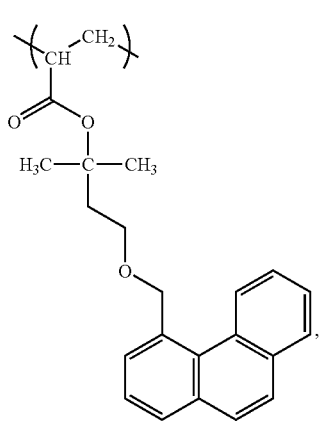

(ii)

a polymer comprising a structural units represented by the formulae (iii) and (iv):

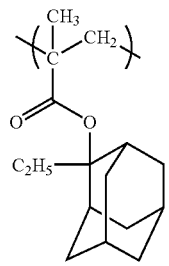

(iii)

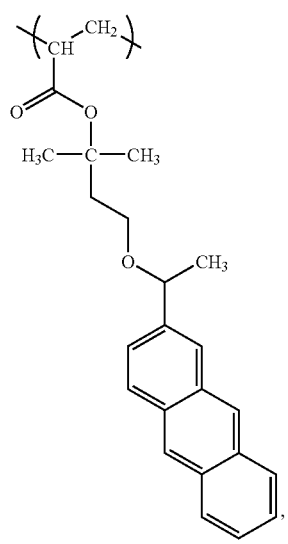

(iv)

a polymer comprising a structural units represented by the formulae (i), (v) and (vi):

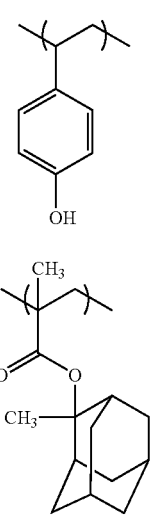

(i)

(v)

a polymer comprising a structural units represented by the formulae (i), (iii) and (vii):

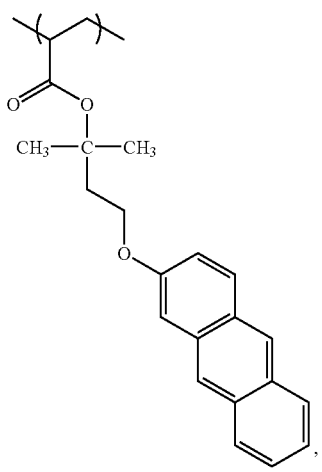
(vi)

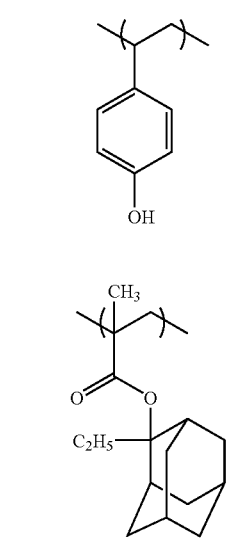
(i)

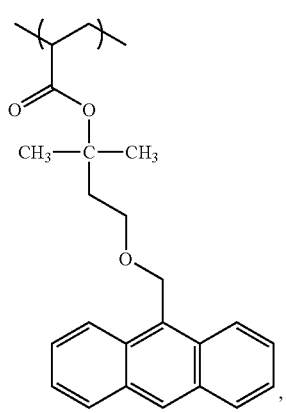
(iii)

(vii)

and a polymer comprising a structural units represented by the formulae (i), (viii) and (ix):

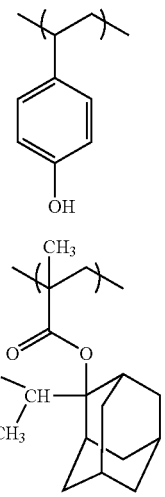
(i)

(viii)

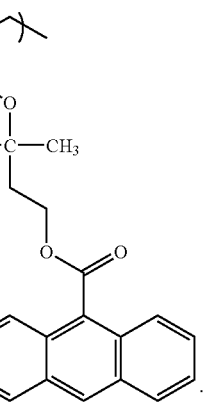
(ix)

The polymer of the present invention itself is insoluble or poorly soluble in an alkali aqueous solution but becomes soluble in an alkali aqueous solution by the action of an acid. The polymer may have other structural unit or units.

The amount of the structural unit derived from the compound represented by the formula (I) is usually 0.1 to 100 moles, preferably 0.1 to 50 moles, more preferably 0.5 to 20 moles, much more preferably 1 to 15 moles, and especially preferably 1 to 10 moles per 100 moles of all the structural units.

The polymer of the present invention may contain the other structural unit or units in addition to the structural unit derived from the compound represented by the formula (I), and the amount of the other structural unit or units is usually 0 to 99.9 moles, preferably 50 to 99.9 moles, more preferably 80 to 99.5 moles, much more preferably 85 to 99 moles, and especially preferably 90 to 99 moles per 100 moles of all the structural units.

When the polymer of the present invention contains the structural unit derived from a styrene having one or more phenolic hydroxyl groups and the structural unit having an acid-labile group in its side chain in addition to the structural unit derived from the compound represented by the formula (I), the ratio of the structural unit derived from a styrene having one or more phenolic hydroxyl groups to the structural unit having an acid-labile group in its side (the structural unit derived from a styrene having one or more phenolic hydroxyl groups/the structural unit having an acid-labile group in its side chain) is usually 99.9/0.1 to 0.1/99.9 and preferably 99/1 to 55/45.

The polymer of the present invention can be produced for example, by conducting a polymerization reaction of the compound represented by the formula (I), a styrene having one or more phenolic hydroxyl groups wherein hydroxyl groups are protected with acetyl groups and the corresponding monomer having an acid-labile group in its side chain followed by hydrolysis.

The polymerization reaction is usually carried out in the presence of a polymerization initiator. Examples of the polymerization initiator include an azo compound such as 2,2'-azobisisobutyronitrile and dimethyl-2,2'-azobis(2-methylpropionate); an organic hydroperoxide such as tert-butyl hydroperoxide and benzoyl peroxide; a redox-type initiator such as hydrogen peroxide/a ferrous salt and benzoyl peroxide/dimethylaniline; an alkyl metal compound such as butyl lithium and triethyl aluminum.

The amount of the polymerization initiator is not limited and it is preferably 1 to 20% by mole based on all monomer or oligomer molar amounts.

The polymerization temperature is usually 0 to 150° C., and preferably 40 to 100° C.

The polymerization reaction is usually carried out in the presence of a solvent and it is preferred to use a solvent which is sufficient to dissolve the monomer, the polymerization initiator and the polymer obtained. Examples thereof include an aromatic hydrocarbon solvent such as benzene, toluene and xylene; an ether solvent such as 1,4-dioxane and tetrahydrofuran; and an alcohol solvent such as methanol, ethanol and isopropyl alcohol. These solvents may be used alone and a mixture thereof may be used. The amount of the solvent is not limited, and practically, it is preferably 1 to 5 parts by weight relative to 1 part of all monomers or oligomers.

After completion of the polymerization reaction, the polymer produced can be isolated, for example, by adding a solvent in which the polymer is insoluble or poorly soluble to the reaction mixture obtained and filtering the precipitated polymer and then, mixing the polymer with an acid such as p-toluenesulfonic acid.

Next, the chemically amplified positive resist composition of the present invention is illustrated.

The resist composition of the present invention comprises the polymer of the present invention, at least one acid generator and at least one solvent.

The polymer comprising the structural unit derived from the compound represented by the formula (I), the structural unit derived from a styrene having one or more phenolic hydroxyl groups and the structural unit having an acid-labile group in its side chain is preferable. The polymer comprising the structural unit derived from the compound represented by the formula (I), the structural unit represented by the formula (II) and the structural unit represented by the formula (III) is more preferable. The polymer comprising the structural unit derived from the compound represented by the formula (I), the structural unit represented by the formula (II) and the structural unit represented by the formula (IIIa) is especially preferable.

The resist composition of the present invention may contain the other polymer or polymers. Examples of the other polymer include a polymer comprising the structural unit derived from a styrene having one or more phenolic hydroxyl groups and the structural unit having an acid-labile group in its side chain, and a polymer comprising the structural unit represented by the formula (II) and the structural unit represented by the formula (III) is preferable.

The content of the polymer of the present invention is preferably 10% by weight or more based on the total weight of the polymer components, and more preferably 50% by weight or more.

The content of the polymer components is usually 60 to 98 parts by weight per 100 parts by weight of the solid components of the composition, and preferably 80 to 95 parts by weight. Hereinafter, "solid components of the composition" means the components other than solvent(s) in the resist composition of the present invention.

The resist composition of the present invention contains at least one acid generator, preferably contains two or more acid generators.

The acid generator generates an acid by irradiation to itself or the composition containing the same, and the acid generated catalytically acts against the polymer of the present invention and/or the other polymer having an acid-labile group, and the polymer of the present invention and/or the other polymer having an acid-labile group become soluble in an aqueous alkali solution.

The acid generator can be selected from various compounds generating the acid by irradiation with radiation on the acid generator itself or the resist composition of the present invention.

As the acid generator, at least one selected from an onium salt, a halogenated alkyltriazine compound, a diazomethane compound having a sulfonyl group, a sulfonate compound and an imide compound having a sulfonyloxy group, is preferable. The onium salt, the diazomethane compound having a sulfonyl group and a mixture thereof are more preferable and a mixture of the onium salt and the diazomethane compound having a sulfonyl group is more preferable. As the onium salt, a sulfonium salt is preferable, and triphenylsulfonium salt is more preferable.

The known acid generator can be used.

Examples of the diazomethane compound having a sulfonyl group include bis(propylsulfonyl)diazomethane, bis(isopropylsulfonyl)diazomethane, bis(butylsulfonyl)diazomethane, bis(tert-butylsulfonyl)diazomethane, bis(cyclopentylsulfonyl)diazomethane, bis(cyclohexylsulfonyl)diazomethane, bis(phenylsulfonyl)diazomethane, bis(4-chlorophenylsulfonyl)diazomethane, bis(p-tolylsulfonyl)diazomethane, bis(4-tert-butylphenylsulfonyl)diazomethane, bis(2,4-xylylsulfonyl)diazomethane, bis(4-isopropylphenylsulfonyl)diazomethane, bis(naphthylsulfonyl)diazomethane, and bis(anthrylsulfonyl)diazomethane.

The content of the acid generator is usually 2 to 40 parts by weight per 100 parts by weight of the solid components of the composition, and preferably 5 to 20 parts by weight.

The resist composition contains at least one solvent, and examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

The content of the solvent is usually 70 to 98 parts by weight per 100 parts by weight of the solid components of the composition, and preferably 85 to 96 parts by weight.

In the resist composition of the present invention, performance deterioration caused by inactivation of acid which occurs due to post exposure delay can be diminished by adding a basic nitrogen-containing organic compound as a quencher.

Specific examples of the nitrogen-containing organic base compound include an amine compound represented by the following formulae:

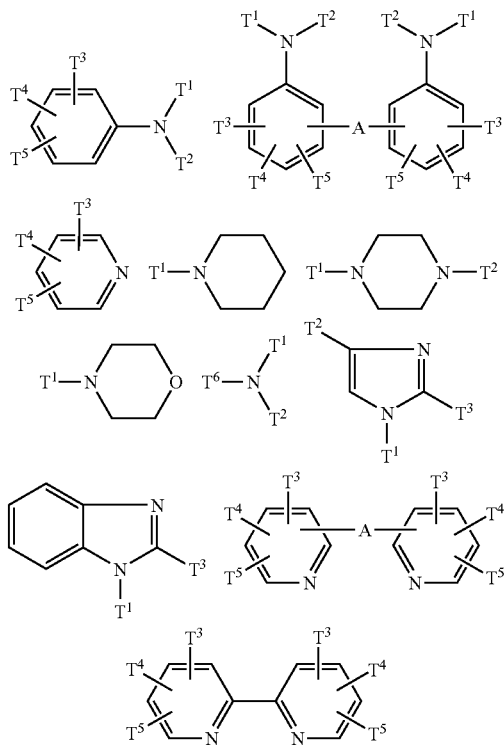

wherein $T^1$ and $T^2$ each independently represent a hydrogen atom, an alkyl group, a cycloalkyl group or an aryl group, and the alkyl, cycloalkyl and aryl groups may have at least one group selected from the group consisting of a hydroxyl group, an amino group which may be substituted with a C1-C4 alkyl group and a C1-C6 alkoxy group which may have a C1-C6 alkoxy group, $T^3$ and $T^4$ each independently represent a hydrogen atom, an alkyl group, a cycloalkyl group, an aryl group or an alkoxy group, and the alkyl, cycloalkyl, aryl and alkoxy groups may have at least one group selected from the group consisting of a hydroxyl group, an amino group which may be substituted with a C1-C4 alkyl group and a C1-C6 alkoxy group, or $T^3$ and $T^4$ bond together with the carbon atoms to which they bond to form an aromatic ring, $T^5$ represents a hydrogen atom, an alkyl group, a cycloalkyl group, an aryl group, an alkoxy group or a nitro group, and the alkyl, cycloalkyl, aryl and alkoxy groups may have at least one group selected from the group consisting of a hydroxyl group, an amino group which may be substituted with a C1-C4 alkyl group and a C1-C6 alkoxy group, $T^6$ represents an alkyl group or a cycloalkyl group, and the alkyl and cycloalkyl groups may have at least one group selected from the group consisting of a hydroxyl group, an amino group which may be substituted with a C1-C4 alkyl group and a C1-C6 alkoxy group, and A represents —CO—, —NH—, —S—, —S—S—, an alkylene group of which at least one methylene group may be replaced by —O—, or an alkenylene group of which at least one methylene group may be replaced by —O—, and a quaternary ammonium hydroxide represented by the following formula:

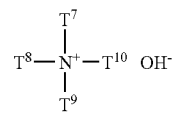

wherein $T^7$, $T^8$, $T^9$ and $T^{10}$ each independently represent an alkyl group, a cycloalkyl group or an aryl group, and the alkyl, cycloalkyl and aryl groups may have at least one group selected from the group consisting a hydroxyl group, an amino group which may be substituted with a C1-C4 alkyl group and a C1-C6 alkoxy group.

The alkyl group in $T^1$, $T^2$, $T^3$, $T^4$, $T^5$, $T^6$, $T^7$, $T^8$, $T^9$ and $T^{10}$ preferably has about 1 to 10 carbon atoms, and more preferably has about 1 to 6 carbon atoms.

Examples of the amino group which may be substituted with the C1-C4 alkyl group include an amino group, a methylamino group, an ethylamino group, an butylamino group, a dimethylamino group and a diethylamino group. Examples of the C1-C6 alkoxy group which may have the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the alkyl group which may have at least one group selected from the group consisting of a hydroxyl group, an amino group which may be substituted with a C1-C4 alkyl group, and a C1-C6 alkoxy group which may have a C1-C6 alkoxy group include a methyl group, an ethyl group, a propyl group, an isopropyl group, a butyl group, a tert-butyl group, a pentyl group, a hexyl group, a octyl group, a nonyl group, a decyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

The cycloalkyl group in $T^1$, $T^2$, $T^3$, $T^4$, $T^5$, $T^6$, $T^7$, $T^8$, $T^9$ and $T^{10}$ preferably has about 5 to 10 carbon atoms. Specific examples of the cycloalkyl group which may have at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

The aryl group in $T^1$, $T^2$, $T^3$, $T^4$, $T^5$, $T^6$, $T^7$, $T^8$, $T^9$ and $T^{10}$ preferably has about 6 to 10 carbon atoms. Specific examples of the aryl group which may have at least one group selected from the group consisting of a hydroxyl group, an amino group which may be substituted with a C1-C4 alkyl group and a C1-C6 alkoxy group include a phenyl group and a naphthyl group.

The alkoxy group in $T^3$, $T^4$ and $T^5$ preferably has about 1 to 6 carbon atoms and specific examples thereof include a methoxy group, an ethoxy group, a propoxy group, an isopropoxy group, a butoxy group, a tert-butoxy group, a pentyloxy group and a hexyloxy group.

The alkylene and alkenylene groups in A preferably have 2 to 6 carbon atoms. Specific examples of the alkylene group include an ethylene group, a trimethylene group, a tetramethylene group, a methylenedioxy group and an ethylene-1,2-dioxy group, and specific examples of the alkenylene group include an ethene-1,2-diyl group, a 1-propene-1,3-diyl group and a 2-butene-1,4-diyl group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptyamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl] amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di(2-pyridyl) ketone, 1,2-di(2-pyridyl) ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, (3-trifluoromethylphenyl) trimethylammonium hydroxide and (2-hydroxyethyl) trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic nitrogen-containing organic compound is used as the quencher, the resist composition of the present invention preferably includes 0.1 to 2 parts by weight of the basic nitrogen-containing organic compound per 100 parts by weight of the solid components, and more preferably 0.2 to 1 parts by weight.

The present resist composition can contain, if necessary, a small amount of various additives such as a sensitizer, a dissolution inhibitor, other polymers, a surfactant, a stabilizer and a dye as long as the effect of the present invention is not prevented.

A resist film applied onto the substrate and then dried is subjected to exposure for patterning, then heat-treated to facilitate a deblocking reaction, and thereafter developed with an alkali developer. The alkali developer used may be any one of various alkaline aqueous solution used in the art. Generally, an aqueous solution of tetramethylammonium hydroxide or (2-hydroxyethyl)trimethylammonium hydroxide (commonly known as "choline") is often used.

It should be construed that embodiments disclosed here are examples in all aspects and not restrictive. It is intended that the scope of the present invention is determined not by the above descriptions but by appended claims, and includes all variations of the equivalent meanings and ranges to the claims.

The present invention will be described more specifically by way of examples, which are not construed to limit the scope of the present invention. The "%" and "part(s)" used to represent the content of any component and the amount of any material used in the following examples and comparative examples are on a weight basis unless otherwise specifically noted. The weight-average molecular weight, the number-average molecular weight of any material used in the following examples is a value found by gel permeation chromatography [HLC-8120GPC Type manufactured by TOSOH CORPORATION, Column (Three Columns): TSKgel Multipore HXL-M, Solvent: tetrahydrofuran] using polystyrene as a standard reference material.

The structures of the obtained compounds used in the following examples were determined by NMR analysis [EX-270 Type or GX-270 Type manufactured by JEOL LTD] and/or mass spectrometry [Liquid Chromatography: 1100 Type, manufactured by Agilent Technologies, Inc., Mass Spectrometry: LC/MSD Type, manufactured by Agilent Technologies, Inc.].

Referential Synthesis Example 1

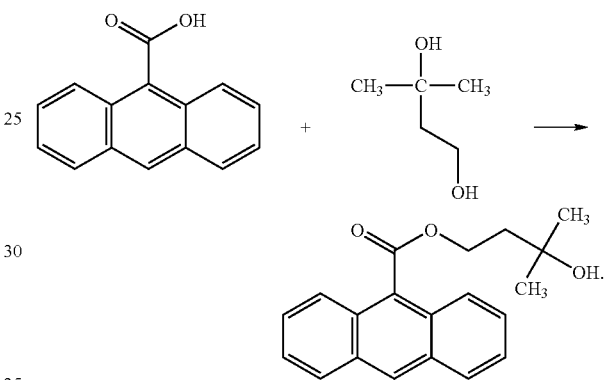

Fifty parts of anthracene-9-carboxylic acid was dissolved in 150 parts of N,N-dimethylformamide. The obtained solution was heated at 50° C. To the solution, a solution obtained by dissolving 36.5 parts of 1,1'-carbonyldiimidazole in 150 parts of N,N-dimethylformamide was added dropwise, and then the obtained solution was stirred at 50° C. for 2 hours. The resultant solution was cooled down to room temperature to obtain a solution (A). A mixture of 11.8 parts of sodium hydride and 141 parts of N,N-dimethylformamide was heated at 50° C. To the mixture, a solution obtained by dissolving 28.1 parts of 2-methyl-butane-2,4-diol in 28 parts of N,N-dimethylformamide was added dropwise and then, the resultant mixture was stirred at 50° C. for 2 hours. The resultant mixture was cooled down to room temperature. To the obtained mixture, the solution (A) was added dropwise at room temperature to obtain a mixture. The obtained mixture was added dropwise to 595 parts of 5% aqueous oxalic acid solution below 30° C. To the resultant mixture, 298 parts of ethyl acetate was added and stirred and then, the obtained mixture was filtrated. The filtrate was separated into an organic layer and an aqueous layer. The aqueous layer was extracted with 298 parts of ethyl acetate and the obtained organic layer was mixed with the organic layer previously obtained. The mixed organic layer was washed five times with ion-exchanged water and then dried over 22.1 parts of magnesium sulfate. The mixture was filtrated and the obtained filtrate was concentrated to obtain 55.6 parts of 3-methyl-3-hydroxybutyl anthracene-9-carboxylate as brown color oil. This compound is called as Compound (C).

$^1$H-NMR (dimethylsulfoxide-$d_6$, internal standard: tetramethylsilane) δ (ppm) 1.17 (s, 6H), 1.94 (t, 2H, J=7.58 Hz), 4.50 (s, 1H), 4.70 (t, 2H, J=6.60 Hz), 7.54-7.66 (m, 4H), 7.97 (d, 2H, J=9.54 Hz), 8.16 (d, 2H, J=9.57 Hz), 8.76 (s, 1H)

Referential Synthesis Example 2

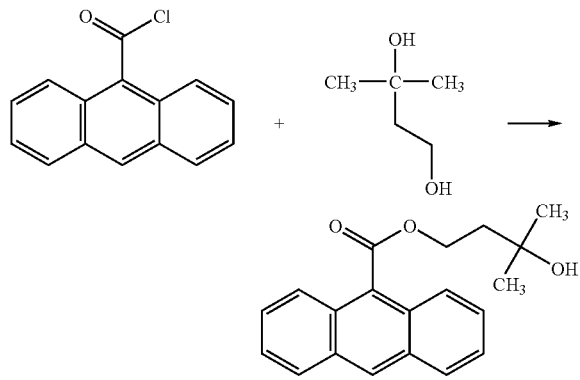

Eighteen point two parts of anthracene-9-carbonyl chloride was dissolved in 182 parts of chloroform, and then, 41.5 parts of pyridine was added thereto. To the obtained mixture, a solution obtained by dissolving 42.1 parts of 2-methyl-butane-2,4-diol in 42 parts of chloroform was added dropwise and then, the resultant mixture was stirred at room temperature overnight and further stirred at 50° C. for 9 hours. The resultant mixture was cooled with ice-bath, and 163 parts of ion-exchanged water was added thereto below 30° C. The obtained mixture was separated into an organic layer and an aqueous layer. The organic layer was washed twice with 163 parts of 2% aqueous oxalic acid solution and then, washed five times with ion-exchanged water. To the obtained organic layer, 4.3 parts of active carbon and 21.7 parts of magnesium sulfate were added to stir and then, the obtained mixture was filtrated. The obtained filtrate was concentrated and the residue was purified with silica gel column chromatography to obtain 11.3 parts of Compound (C) as orange color oil.

Example 1

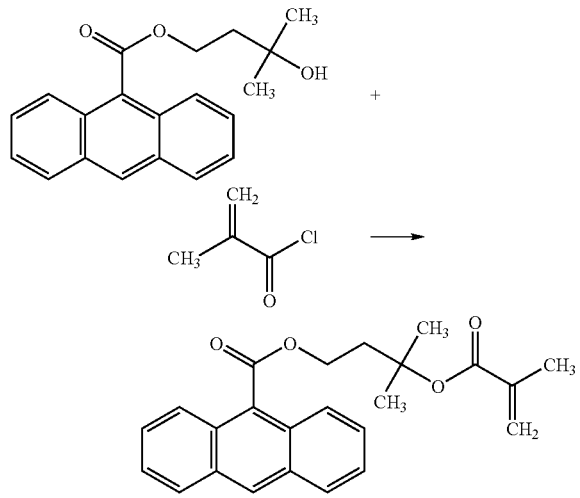

Forty four point two parts of Compound (C) was dissolved in 133 parts of methyl isobutyl ketone, and 1.8 parts of active carbon was added to the obtained solution to stir at room temperature for 1 hour. The mixture was filtrated and the filtrate was concentrated. To the residue, 160 parts of methyl isobutyl ketone and 25 parts of 1-methylpyrrolidine were added and the resultant mixture was heated at 50° C. To the mixture, 18.4 parts of methacryloyl chloride was added dropwise, and the resultant mixture was stirred at 50° C. for 6 hours. To the mixture, 8.3 parts of 1-methylpyrrolidine was added and then, 6.1 parts of methacryloyl chloride was added, and the resultant mixture was stirred at 50° C. for 4 hours. The reaction mixture was cooled with ice-bath and 441 parts of 2% aqueous oxalic acid solution was added dropwise thereto and then, the resultant mixture was separated into an organic layer and an aqueous layer. The aqueous layer was extracted twice with 92 parts of methyl isobutyl ketone, and the obtained organic layers were mixed with the organic layer previously obtained. The mixed organic layer was washed seven times with ion-exchanged water. To the obtained organic layer, 4.2 parts of active carbon was added to stir and then, the obtained mixture was filtrated. The obtained filtrate was concentrated and the residue was purified with silica gel column chromatography to obtain 39 parts of 3-methyl-3-methacryloyloxybutyl anthracene-9-carboxylate as yellow color oil. This compound is called as Compound (E).

$^1$H-NMR (dimethylsulfoxide-$d_6$, internal standard: tetramethylsilane) δ (ppm) 1.51 (s, 6H), 1.68 (s, 3H), 2.34 (t, 2H, J=6.19 Hz), 4.70 (t, 2H, J=7.24 Hz), 5.40 (t, 1H, J=1.65 Hz), 5.58 (t, 1H, J=0.97 Hz), 7.54-7.65 (m, 4H), 7.97 (d, 2H, J=9.56 Hz), 8.15 (d, 2H, J=8.88 Hz), 8.76 (s, 1H)

Referential Synthesis Example 3

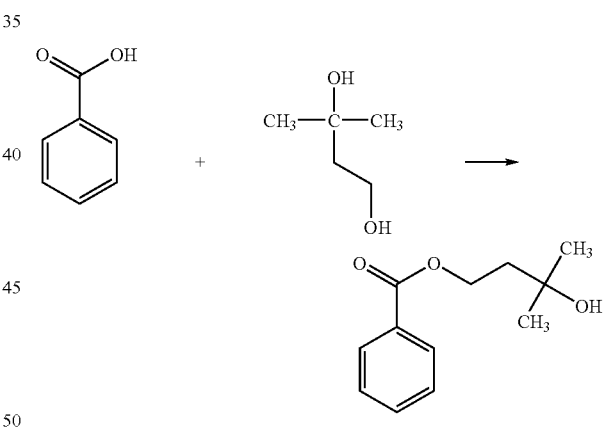

Three parts of benzoic acid was mixed with 2.6 parts of 2-methyl-butane-2,4-diol, 0.6 part of 4-dimethylaminopyridine and 45 parts of dehydrated tetrahydrofuran. To the obtained mixture, 5.6 parts of N,N'-dicyclohexylcarbodiimide was added, and then the obtained mixture was stirred at room temperature for 24 hours. The resultant mixture was filtrated and the filtrate was concentrated. To the residue, 33 parts of methyl tert-butyl ether was added and then, 17 parts of 2% aqueous oxalic acid solution was added. The resultant mixture was stirred and filtrated. The filtrate was separated into an organic layer and an aqueous layer. The organic layer was washed five times with ion-exchanged water and then dried over 3.1 parts of magnesium sulfate. The mixture was filtrated and the obtained filtrate was concentrated. The obtained residue was mixed with 6 parts of methyl tert-butyl ether and the resultant mixture was filtrated. The filtrate was concentrated to obtain 4.8 parts of 3-methyl-3-hydroxybutyl benzoate as colorless oil. This compound is called as Compound (G).

$^1$H-NMR (dimethylsulfoxide-$d_6$, internal standard: tetramethylsilane) δ (ppm) 1.16 (s, 6H), 1.82 (t, 2H, J=7.08 Hz), 4.37 (s, 2H, J=6.94 Hz), 4.41 (s, 1H), 7.48-7.53 (m, 2H), 7.60-7.67 (m, 1H), 7.93-7.96 (m, 2H)

Example 2

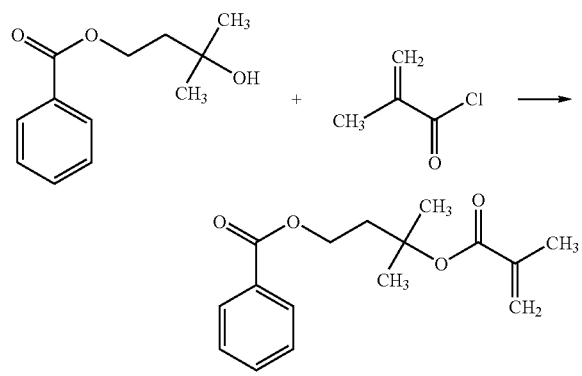

Thirty eight point nine parts of Compound (G) and 39.8 parts of 1-methylpyrrolidine were dissolved in dehydrated tetrahydrofuran. The obtained solution was heated at 50° C. To the solution, 29.3 parts of methacryloyl chloride was added dropwise, and the resultant mixture was stirred at 50° C. for 7 hours. The reaction mixture was cooled with ice-bath and 101 parts of ion-exchanged water and 101 parts of ethyl acetate were added thereto and then, the resultant mixture was separated into an organic layer and an aqueous layer. The aqueous layer was extracted twice with 101 parts of ethyl acetate, and the obtained organic layers were mixed with the organic layer previously obtained. The mixed organic layer was washed three times with 2% aqueous oxalic acid solution and then, washed eight times with ion-exchanged water. To the obtained organic layer, 3.9 parts of active carbon was added to stir and then, the obtained mixture was filtrated. The obtained filtrate was concentrated and the residue was purified with silica gel column chromatography to obtain 43.8 parts of 3-methyl-3-methacryloyloxybutyl benzoate as colorless oil. This compound is called as Compound (H).

$^1$H-NMR (dimethylsulfoxide-$d_6$, internal standard: tetramethylsilane) δ (ppm) 1.51 (s, 6H), 1.77-1.78 (m, 3H), 2.26 (t, 2H, J=6.62 Hz), 4.39 (t, 2H, J=6.59 Hz), 5.54-5.55 (m, 1H), 5.92-5.93 (m, 1H), 7.47-7.53 (m, 2H), 7.61-7.67 (m, 1H), 7.91-7.95 (m, 2H)

MS (ESI (+) Spectrum): [M+Na]$^+$=299.1 ($C_{16}H_{20}O_4$ Na$^+$=299.32)

Example 3

The inner gas of a four-necked flask equipped with a stirrer, a condenser and a thermometer was replaced by nitrogen gas. To the flask, 3.6 parts of 2-ethyl-2-adamantyl methacrylate, 11.8 parts of 4-(1-ethoxyethoxy)styrene, 1.6 parts of Compound (E) and 23.2 parts of methyl isobutyl ketone were added and the obtained mixture was heated at 80° C. To the mixture, a solution obtained by dissolving 0.8 part of dimethyl 2,2'-azobis(2-methylpropionate) in 2.2 parts of methyl isobutyl ketone was added dropwise over 10 minutes. The resultant mixture was kept at 80° C. for 15 hours. The obtained reaction mixture was added dropwise to a solution of 350 parts of methanol and 43 parts of water. The precipitated polymer was obtained by filtration. The polymer was dissolved in 51 parts of methyl isobutyl ketone, and 0.3 part of p-toluenesulfonic acid and 34 parts of water were added thereto. The resultant mixture was stirred at room temperature for 5 hours. The mixture was subjected to a separation and washing procedure and this procedure was repeated. The obtained organic layer was concentrated and the obtained residue was mixed with propylene glycol methyl ether acetate. The obtained solution was concentrated to obtain a solution containing a polymer. This polymer is called as Polymer (J1). The weight-average molecular weight (Mw) of Polymer (J1) was 6,000 and the degree of dispersion (Mw/Mn) of Polymer (J1) was 1.60. The content of the structural unit derived from Compound (E) in polymer (J1) was 5 moles per 100 moles of all the structural units of Polymer (J1).

Polymer (J1) comprises the following structural units.

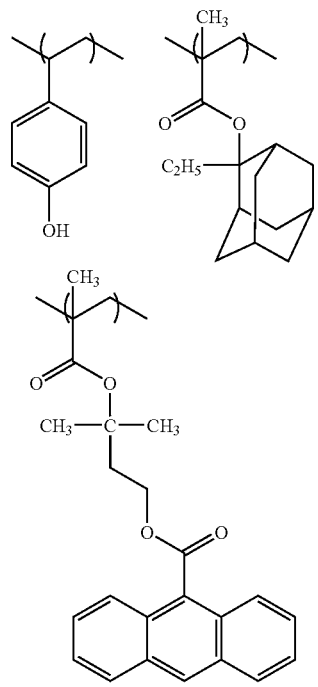

Example 4

The inner gas of a four-necked flask equipped with a stirrer, a condenser and a thermometer was replaced by nitrogen gas. To the flask, 3.1 parts of 2-ethyl-2-adamantyl methacrylate, 9.7 parts of 4-(1-ethoxyethoxy)styrene, 2.8 parts of Compound (E) and 21.2 parts of methyl isobutyl ketone were added and the obtained mixture was heated at 80° C. To the mixture, a solution obtained by dissolving 0.7 part of dimethyl 2,2'-azobis(2-methylpropionate) in 1.9 parts of methyl isobutyl ketone was added dropwise over 10 minutes. The resultant mixture was kept at 80° C. for 15 hours. The obtained reaction mixture was added dropwise to a solution of 320 parts of methanol and 40 parts of water. The precipitated polymer was obtained by filtration. The polymer was dissolved in 46 parts of methyl isobutyl ketone, and 0.3 part of p-toluenesulfonic acid and 31 parts of water were added thereto. The resultant mixture was stirred at room temperature for 5 hours. The mixture was subjected to a separation and washing procedure and this procedure was repeated. The obtained organic layer was concentrated and the obtained residue was mixed with propylene glycol methyl ether acetate. The obtained solution was concentrated to obtain a solution containing a polymer. This polymer is called as Polymer (J2). The weight-average molecular weight (Mw) of Polymer (J2) was 8,200 and the degree of dispersion (Mw/Mn) of Polymer (J2) was 1.78. The content of the structural unit derived from Compound (E) in polymer (J2) was 10 moles per 100 moles of all the structural units of Polymer (J2).

Polymer (J2) comprises the following structural units.

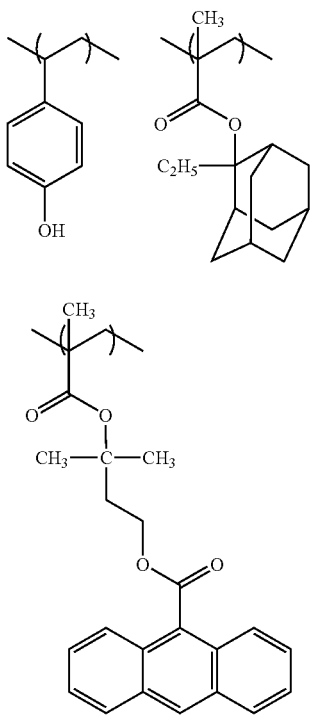

Example 5

The inner gas of a four-necked flask equipped with a stirrer, a condenser and a thermometer was replaced by nitrogen gas. To the flask, 3.7 parts of 2-ethyl-2-adamantyl methacrylate, 14.4 parts of 4-(1-ethoxyethoxy)styrene, 2.8 parts of Compound (H) and 28.6 parts of methyl isobutyl ketone were added and the obtained mixture was heated at 80° C. To the mixture, a solution obtained by dissolving 1.0 part of dimethyl 2,2'-azobis(2-methylpropionate) in 2.8 parts of methyl isobutyl ketone was added dropwise over 10 minutes. The resultant mixture was kept at 80° C. for 15 hours. The obtained reaction mixture was added dropwise to a solution of 430 parts of methanol and 53 parts of water. The precipitated polymer was obtained by filtration. The polymer was dissolved in 63 parts of methyl isobutyl ketone, and 0.4 part of p-toluenesulfonic acid and 42 parts of water were added thereto. The resultant mixture was stirred at room temperature for 1 hour. The mixture was subjected to a separation and washing procedure and this procedure was repeated. The obtained organic layer was concentrated and the obtained residue was mixed with propylene glycol methyl ether acetate. The obtained solution was concentrated to obtain a solution containing a polymer. This polymer is called as Polymer (J5). The weight-average molecular weight (Mw) of Polymer (J5) was 6,900 and the degree of dispersion (Mw/Mn) of Polymer (J5) was 1.62. The content of the structural unit derived from Compound (H) in polymer (J5) was 10 moles per 100 moles of all the structural units of Polymer (J5).

Polymer (J5) comprises the following structural units.

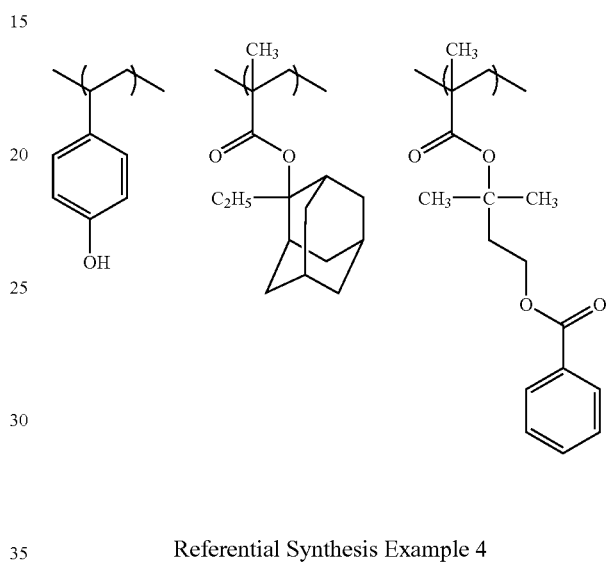

Referential Synthesis Example 4

Into a flask, 103.8 parts of 4-acetoxystyrene, 39.7 parts of 2-ethyl-2-adamantyl methacrylate and 265 parts of isopropanol were charged. The resultant solution was heated to 75° C. under an atmosphere of nitrogen, and then, a solution prepared by dissolving 11.05 parts of dimethyl-2,2'-azobis(2-methylpropionate) in 22.11 parts of isopropanol was added dropwise to the mixture. The resultant mixture was refluxed for 12 hours. The reaction mixture obtained was cooled and was poured into a large amount of methanol. The precipitated polymer was collected by filtration to obtain 250 parts of a polymer. The obtained polymer was contained methanol.

Into a flask, 250 parts of the obtained polymer, 202 parts of methanol and 10.3 parts of 4-dimethylaminopyridine were charged and the resultant mixture was refluxed for 20 hours. The obtained mixture was cooled and then, was mixed with 7.6 parts of glacial acetic acid. The mixture obtained was poured into a large amount of water and the precipitated polymer was collected by filtration. The polymer was dissolved in acetone and the solution obtained was poured into a large amount of water to precipitate a resin. This operation was repeated three times to obtain 95.9 parts of a polymer. This polymer is called as Polymer (J3). The weight-average molecular weight (Mw) of Polymer (J3) was about 8,600. Polymer (J3) comprises the following structural units, and the ratio of the structural unit derived from 2-ethyl-2-adamantyl methacrylate to the structural unit derived from 4-hydroxystyrene (the structural unit derived from 2-ethyl-2-adamantyl methacrylate/the structural unit derived from 4-hydroxystyrene) was about 20/80 from the result of $^{13}$C-NMR analysis.

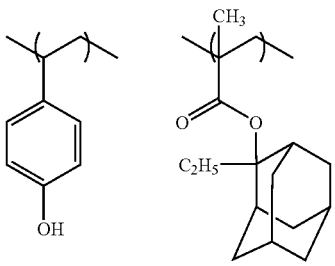

Referential Synthesis Example 5

A reaction was conducted according to the same manner as Referential Synthesis Example 4 expect that 59.6 parts of 2-ethyl-2-adamantyl methacrylate was used in place of 39.7 parts of 2-ethyl-2-adamantyl methacrylate, and 90.8 parts of 4-acetoxystyrene was used in place of 103.8 parts of 4-acetoxystyrene. As the result, 102.8 parts of a polymer was obtained. This polymer is called as Polymer (J4). The weight-average molecular weight (Mw) of Polymer (J4) was about 8,200. Polymer (J4) comprises the following structural units, and the ratio of the structural unit derived from 2-ethyl-2-adamantyl methacrylate to the structural unit derived from 4-hydroxystyrene (the structural unit derived from 2-ethyl-2-adamantyl methacrylate/the structural unit derived from 4-hydroxystyrene) was about 30/70 from the result of $^{13}$C-NMR analysis.

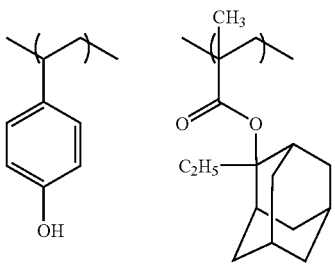

Examples 6 to 10 and Comparative Example 1

Acid Generator

Acid generator K1: triphenylsulfonium 2,4,6-triisopropylbenzenesulfonate
Acid generator K2: bis(cyclohexylsulfonyl)diazomethane
<Quencher>
Quencher L1: 2,6-diisopropylaniline
<Additives>
Additives M1: polypropylene glycol (molecular weight: 2000)
<Solvent>
Solvent S1: propylene glycol monomethyl ether acetate/propylene glycol monomethyl ether (weight ratio=4/1)

The following components were mixed to give a solution, and the solution was further filtrated through a fluorine resin filter having a pore diameter of 0.2 µm, to prepare resist liquid.
Polymer (kind and amount are described in Table 1)
Acid generator (kind and amount are described in Table 1)
Quencher (kind and amount are described in Table 1)
Additives (kind and amount are described in Table 1)
Solvent (kind and amount are described in Table 1)

TABLE 1

| Ex. No. | Polymer (kind/ amount (part)) | Acid generator (kind/amount (part)) | Quencher (kind/ amount (part)) | Solvent (kind/ amount (part)) | Additives (kind/ amount (part)) |
|---|---|---|---|---|---|
| Ex. 6 | J1/90.6 | K1/3.0 K2/6.0 | L1/0.4 | S1/1207 | M1/9.0 |
| Ex. 7 | J1/45.3 J2/45.3 | K1/3.0 K2/6.0 | L1/0.4 | S1/1207 | M1/9.0 |
| Ex. 8 | J2/45.3 | K1/3.0 K2/6.0 | L1/0.4 | S1/1207 | M1/9.0 |
| Ex. 9 | J2/54.4 J3/36.2 | K1/3.0 K2/6.0 | L1/0.4 | S1/1207 | M1/9.0 |
| Ex. 10 | J5/90.6 | K1/3.0 K2/6.0 | L1/0.4 | S1/1207 | M1/9.0 |
| Comp. Ex. 1 | J3/45.3 J4/45.3 | K1/3.0 K2/3.0 | L1/0.37 | S1/1207 | M1/9.0 |

Each of the resist liquids prepared as above was spin-coated over the silicon wafer on which a silicon dioxide film of 100 nm thickness was formed. After coating each of the resist liquids, the silicon wafers thus coated with the respective resist liquids were each prebaked on a proximity hotplate at a temperature of 90° C. for 60 seconds to form resist film of which thickness was 200 nm. Using a KrF excimer laser stepper ("NSR-2205EX12B" manufactured by Nikon Corporation, NA=0.55, σ=0.80), each wafer on which the respective resist film had been thus formed was exposed via several masks having different shapes and size.

After the exposure, each wafer was subjected to post-exposure baking on a hotplate at a temperature of 110° C. for 60 seconds and then to paddle development for 60 seconds with an aqueous solution of 2.38% tetramethylammonium hydroxide.

Each of a pattern developed on the substrate after the development was observed with a scanning electron microscope, and the results of which are shown in Table 2.

Effective Sensitivity (ES): It is expressed as the amount of exposure that the line and space pattern become 1:1 after exposure through 250 nm line and space pattern mask and development.

Resolution: It is expressed as the minimum size of space pattern which gave the space pattern split by the line pattern at the exposure amount of the effective sensitivity.

Profile: Each of a wall surface of pattern developed on the organic anti-reflective coating substrate after the development was observed with a scanning electron microscope. When the wall surface was a waved pattern, its evaluation was marked by "X", when the wall surface was flat or nearly flat pattern, its evaluation was marked by "○".

TABLE 2

| Ex. No. | Profile | Resolution (nm) |
|---|---|---|
| Ex. 6 | ○ | 190 |
| Ex. 7 | ○ | 190 |
| Ex. 8 | ○ | 200 |
| Ex. 9 | ○ | 190 |
| Ex. 10 | ○ | 200 |
| Comp. Ex. 1 | X | 220 |

The chemically amplified positive resist composition of the present invention gives patterns having high resolution and good profile and is suitable for KrF lithography, ArF lithography, EUV (extreme ultraviolet) lithography and EB (electron beam) lithography.

What is claimed is:

1. A compound represented by the formula (I):

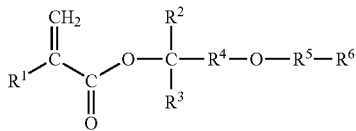

wherein $R^1$ represents a hydrogen atom, a fluorine atom, a C1-C4 linear or branched chain alkyl group or a C1-C4 fluorinated linear or branched chain alkyl group, $R^2$ and $R^3$ each independently represent a C1-C4 linear or branched chain alkyl group, $R^4$ represents a C1-C8 divalent hydrocarbon group, $R^5$ represents a single bond, a C1-C4 divalent hydrocarbon group or a carbonyl group, and $R^6$ represents an anthryl group which may have a C1-C6 linear or branched chain alkyl group or a C1-C6 linear or branched chain alkoxy group.

2. The compound according to claim 1, wherein the anthryl group is a 9-anthryl group.

3. A polymer comprising a structural unit derived from a compound represented by the formula (I):

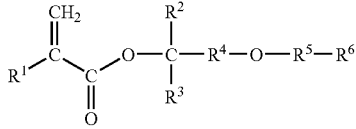

wherein $R^1$ represents a hydrogen atom, a fluorine atom, a C1-C4 linear or branched chain alkyl group or a C1-C4 fluorinated linear or branched chain alkyl group, $R^2$ and $R^3$ each independently represent a C1-C4 linear or branched chain alkyl group, $R^4$ represents a C1-C8 divalent hydrocarbon group, $R^5$ represents a single bond, a C1-C4 divalent hydrocarbon group or a carbonyl group, and $R^6$ represents an anthryl group which may have a C1-C6 linear or branched chain alkyl group or a C1-C6 linear or branched chain alkoxy group.

4. The polymer according to claim 3, wherein the polymer further comprises a structural unit derived from a styrene having one or more phenolic hydroxyl groups.

5. The polymer according to any one of claim 3 or 4, wherein the polymer further comprises a structural unit having an acid-labile group in its side chain.

6. The polymer according to claim 5, wherein the structural unit having an acid-labile group in its side chain is a structural unit represented by the formula (III):

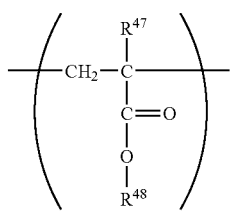

wherein $R^{47}$ represents a hydrogen atom, a fluorine atom, a C1-C4 linear or branched chain alkyl group or a C1-C4 fluorinated linear or branched chain alkyl group, and $R^{48}$ represents a group represented by the following formula:

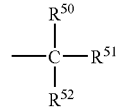

$R^{50}$, $R^{51}$ and $R^{52}$ each independently represent a C1-C6 alkyl group or a C3-C12 alicyclic hydrocarbon group, and $R^{51}$ and $R^{52}$ may be bonded to form a C3-C20 cyclic hydrocarbon group which may be substituted.

7. The polymer according to claim 4, wherein the structural unit derived from a styrene having one or more phenolic hydroxyl groups is a structural unit represented by the formula (II):

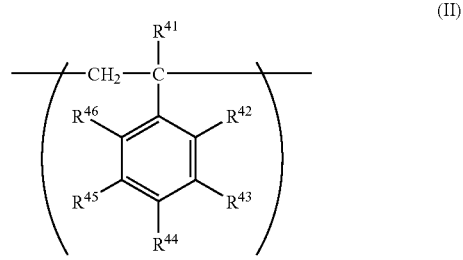

wherein $R^{41}$ represents a hydrogen atom, a fluorine atom, a C1-C4 linear or branched chain alkyl group or a C1-C4 fluorinated linear or branched chain alkyl group, $R^{42}$, $R^{43}$, $R^{44}$, $R^{45}$ and $R^{46}$ each independently represent a hydrogen atom, a hydroxyl group or a C1-C4 linear or branched chain alkyl group, with the proviso that one to three groups among $R^{42}$ to $R^{46}$ are hydroxyl groups and zero to two groups among $R^{42}$ to $R^{46}$ are C1-C4 linear or branched chain alkyl groups.

8. The polymer according to claim 4, wherein the content of the structural unit represented by the formula (I) is 0.1 to 50 moles per 100 moles of all the structural units.

9. A chemically amplified positive resist composition comprising a polymer that comprises a structural unit derived from a compound represented by the formula (I):

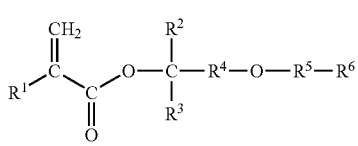

wherein $R^1$ represents a hydrogen atom, a fluorine atom, a C1-C4 linear or branched chain alkyl group or a C1-C4 fluorinated linear or branched chain alkyl group, $R^2$ and $R^3$ each independently represent a C1-C4 linear or branched chain alkyl group, $R^4$ represents a C1-C8 divalent hydrocarbon group, $R^5$ represents a single bond, a C1-C4 divalent hydrocarbon group or a carbonyl group, and $R^6$ represents an anthryl group which may have a C1-C6 linear or branched chain alkyl group or a C1-C6 linear or branched chain alkoxy group, at least one acid generator which comprises a diazomethane compound having a sulfonyl group, and at least one solvent.

10. The chemically amplified positive resist composition according to claim 9, wherein the chemically amplified positive resist composition further comprises a basic nitrogen-containing organic compound.

* * * * *